US012642794B2

(12) United States Patent
Biglan et al.

(10) Patent No.: US 12,642,794 B2
(45) Date of Patent: Jun. 2, 2026

(54) DOSE REGIMENS FOR USE OF LY3154207 IN THE TREATMENT OF DOPAMINERGIC CNS DISORDERS

(71) Applicant: Eli Lilly and Company, Indianapolis, IN (US)

(72) Inventors: Kevin Michael Biglan, Indianapolis, IN (US); Christina Marie Kiley, Indianapolis, IN (US); Kjell Anders Ivan Svensson, Indianapolis, IN (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 1010 days.

(21) Appl. No.: 17/416,320

(22) PCT Filed: Dec. 16, 2019

(86) PCT No.: PCT/US2019/066465
§ 371 (c)(1),
(2) Date: Jun. 18, 2021

(87) PCT Pub. No.: WO2020/131671
PCT Pub. Date: Jun. 25, 2020

(65) Prior Publication Data

US 2022/0062265 A1 Mar. 3, 2022

Related U.S. Application Data

(60) Provisional application No. 62/781,251, filed on Dec. 18, 2018, provisional application No. 62/904,048, filed on Sep. 23, 2019.

(51) Int. Cl.
*A61K 31/472* (2006.01)
*A61P 25/16* (2006.01)
*A61P 25/28* (2006.01)

(52) U.S. Cl.
CPC ............ *A61K 31/472* (2013.01); *A61P 25/16* (2018.01); *A61P 25/28* (2018.01)

(58) Field of Classification Search
CPC ......... A61K 31/472; A61P 25/28; A61P 25/16
See application file for complete search history.

(56) References Cited

U.S. PATENT DOCUMENTS

| | | | | |
|---|---|---|---|---|
| 8,962,654 | B2 * | 2/2015 | Beadle | A61P 25/18 514/307 |
| 10,611,751 | B2 | 4/2020 | Hilliard | |
| 2017/0231937 | A1 | 8/2017 | Bolsoy | |
| 2023/0382869 | A1 * | 11/2023 | Hao | A61P 25/16 |
| 2024/0165101 | A1 * | 5/2024 | Biglan | A61K 31/198 |

FOREIGN PATENT DOCUMENTS

| | | | | |
|---|---|---|---|---|
| CA | 3139622 | | 1/2021 | |
| WO | 2014193781 | | 12/2014 | |
| WO | WO-2014193781 | A1 * | 12/2014 | A61P 25/00 |
| WO | 2017070068 | A1 | 4/2017 | |
| WO | 2019204418 | | 10/2019 | |
| WO | 2020257043 | | 12/2020 | |
| WO | 2021001288 | | 1/2021 | |
| WO | 2022076418 | | 4/2022 | |
| WO | 2022192231 | | 9/2022 | |
| WO | 2022192255 | | 9/2022 | |

OTHER PUBLICATIONS

Nair et al. (Journal of Basic and Clinical Pharmacy. vol. 7 Issue 2 Mar.-May 2016. p. 27-31) (Year: 2016).*
Lee et al. (Molecular Neurobiology (2018) 55:5658-5671) (Year: 2018).*
Biglan (Movement Disorders, vol. 37, No. 3, 2022. p. 513-524) (Year: 2022).*
Aarsland D, et al. Are Parkinson's disease with dementia and dementia with Lewy bodies the same entity? J Geriatr Psychiatry Neurol. 2004; 17(3):137-145.
Ballard C, et al. Differences in neuropathologic characteristics across the Lewy body dementia spectrum. Neurology. 2006;67(11):1931-1934.
Berg D, et al. Time to redefine PD? Introductory statement of the MDS Task Force on the definition of Parkinson's disease. Mov Disord. 2014;29(4):454-462.
Biglan, K., et al. "A D1 receptor positive allosteric modulator (LY3154207) enhances wakefulness in sleep deprived healthy volunteers (P3. 6-041)." (2019). Retrieved from the Internet:URL:https://n.neurology.org/content/92/15_Supplement/P3.6-041.
Emre M, et al. Rivastigmine for dementia associated with Parkinson's disease. N Engl J Med. 2004;351(24):2509-2518.
Hembre, E. J., et al. "The discovery of novel dopamine D1 positive allosteric modulators for the treatment of neurodegenerative disorders." 7th RSC/SCI Symposium on GPCRs in Medicinal Chemistry, Verona, Italy. 2018.
International Searching Authority. International Search Report and Written Opinion for application PCT/US2019/066465. Mailed on Mar. 11, 2020. 16 pages.

(Continued)

*Primary Examiner* — Kortney L. Klinkel
*Assistant Examiner* — Richard Grant Peckham
(74) *Attorney, Agent, or Firm* — Elias C. Sayre

(57) ABSTRACT

The present invention relates to dosing regimens and methods of using LY3154207, also described as 2-(2,6-dichlorophenyl)-1-[(1S,3R)-3-(hydroxymethyl)-5-(3-hydroxy-3-methylbutyl)-1-methyl-3,4-dihydroisoquinolin-2 (1H)-yllethanone, and/or pharmaceutical compositions thereof, for treatment of dopaminergic central nervous system disorders. Dopaminergic CNS disorders of the present dosing regimen methods include Parkinson's Disease, Alzheimer's Disease, Lewy body dementia (LBD), Vascular Dementia, Schizophrenia, ADHD, Depression, Autism, chronic musculoskeletal pain, fibromyalgia, cognitive impairment disorders, sleep disorders, excessive daytime sleepiness, narcolepsy, shift work disorder, traumatic brain injury, chronic traumatic encephalopathy, obesity and appetite regulation, mood disorders, lethargy, apathy, and addiction disorders.

25 Claims, 9 Drawing Sheets

(56) References Cited

OTHER PUBLICATIONS

Johansen KK, et al. Biomarkers: Parkinson disease with dementia and dementia with Lewy bodies. Parkinsonism Relat Disord. 2010;16(5):307-315.
Lippa CF, et al. DLB and PDD boundary issues: diagnosis, treatment, molecular pathology, and biomarkers. Neurology. 2007;68(11):812-819.
Mckeith IG, et al. Diagnosis and management of dementia with Lewy bodies: third report of the DLB Consortium. Neurology. 2005;65(12):1863-1872.
Postuma RB, et al. Idiopathic REM sleep behavior disorder in the transition to degenerative disease. Mov Disord. 2009;24(15):2225-2232.
Postuma RB, et al. MDS clinical diagnostic criteria for Parkinson's disease. Mov Disord. 2015;30(12):1591-1601.
Sheikh JI, et al. Geriatric Depression Scale (GDS): Recent evidence and development of a shorter version. Clin Gerontologist. 1986;5:165-173.
Trzepacz PT, et al. Alzheimer's Disease Neuroimaging Initiative. Relationship between the Montreal Cognitive Assessment and Mini-mental State Examination for assessment of mild cognitive impairment in older adults. BMC Geriatr. 2015;15:107.
Yesavage JA, et al. Development and validation of a geriatric depression screening scale: A preliminary report. J Psychiatr Res. 1983;17:37-49.
Biglan et al., "Safety and Efficacy of Mevidalen in Lewy Body Dementia: A phase II, Randomized, Placebo Controlled Trial", Movement Disorders, vol. 37., No. 3, p. 513-524, 2022.
Hao, et al., "Synthesis and Pharmacological Characterization of 2-(2,6-Dichlorophenyl)-1-((1S,3R)-5-(3-hydroxy-3-methylbutyl)-3-(hydroxymethyl)-1-methyl-3,4-dihydroisoquinolin-2(1H)-yl)ethan-1-one (LY3154207), a Potent, Subtype Selective, and Orally Available Positive Allosteric Modulator of the Human Dopamine D1 Receptor", J. Med. Chem. 2019, 62, 8711-8732.
McCarthy, et al., "The Dopamine D1 Receptor Positive Allosteric Modulator Mevidalen (LY3154207) Enhances Wakefulness in the Humanized D1 Mouse and in Sleep-Deprived Healthy Male Volunteers", J Pharmacol Exp Ther 380:143-152, 2022.
Reagan-Shaw, S., Nihal, M., Ahmad, N. "Dose translation from animal to human studies revisited", FASEB J. 22, 659- 661 (2007).
Wang, et al., ""Evaluating the Use of Digital Biomarkers to Test Treatment Effects on Cognition andMovement in Patients with Lewy Body Dementia"", Journal of Parkinson's Disease 12 (2022) 1991-2004.
Wilbraham, et al., ""Safety, Tolerability, and Pharmacokinetics of Mevidalen (LY3154207), a Centrally ActingDopamine D1 Receptor—Positive Allosteric Modulator, in Patients With Parkinson Disease"", Clinical Pharmacology in Drug Development, 2022, 11(3) 324-332.
Wilbraham, et al., "Safety, Tolerability, and Pharmacokinetics of Mevidalen (LY3154207), a Centrally Acting Dopamine D1 Receptor-Positive Allosteric Modulator (D1PAM), in Healthy Subjects", Clinical Pharmacology in Drug Development 2021, 10(4) 393-403.
Kaar Stephen J, et al: "Antipsychotics: Mechanisms underlying clinical response and side-effects and novel treatment approaches based on pathophysiology", Neuropharmacology, Elsevier, Amsterdam, NL, vol. 172, Jul. 9, 2019 (Jul. 9, 2019), XP086171220, ISSN: 0028-3908, DOI: 10.1016/J.NEUROPHARM.2019.107704.

* cited by examiner

Part B (Participants With PD)

Cohort 5 (N=12)
8 LY 75 mg; 4 PBO

Safety data review

Cohort 6 (LY 75 mg Titration)
(N=12)
8 LY titrated dose[b]; 4 PBO

Admission to CRU 2 days prior to first dose

R

Part A (Healthy Subjects)

Cohort 1 (N=12)
9 LY 15 mg; 3 PBO

Safety data to at least Day 7[a]

Cohort 2 (N=12)
9 LY 30 mg; 3 PBO

Safety data to at least Day 7[a]

Cohort 3 (N=12)
9 LY 75 mg; 3 PBO

Safety data to at least Day 7[a]

Cohort 4 (N=12)
9 LY 150 mg; 3 PBO

Admission to CRU 2 days prior to first dose

R

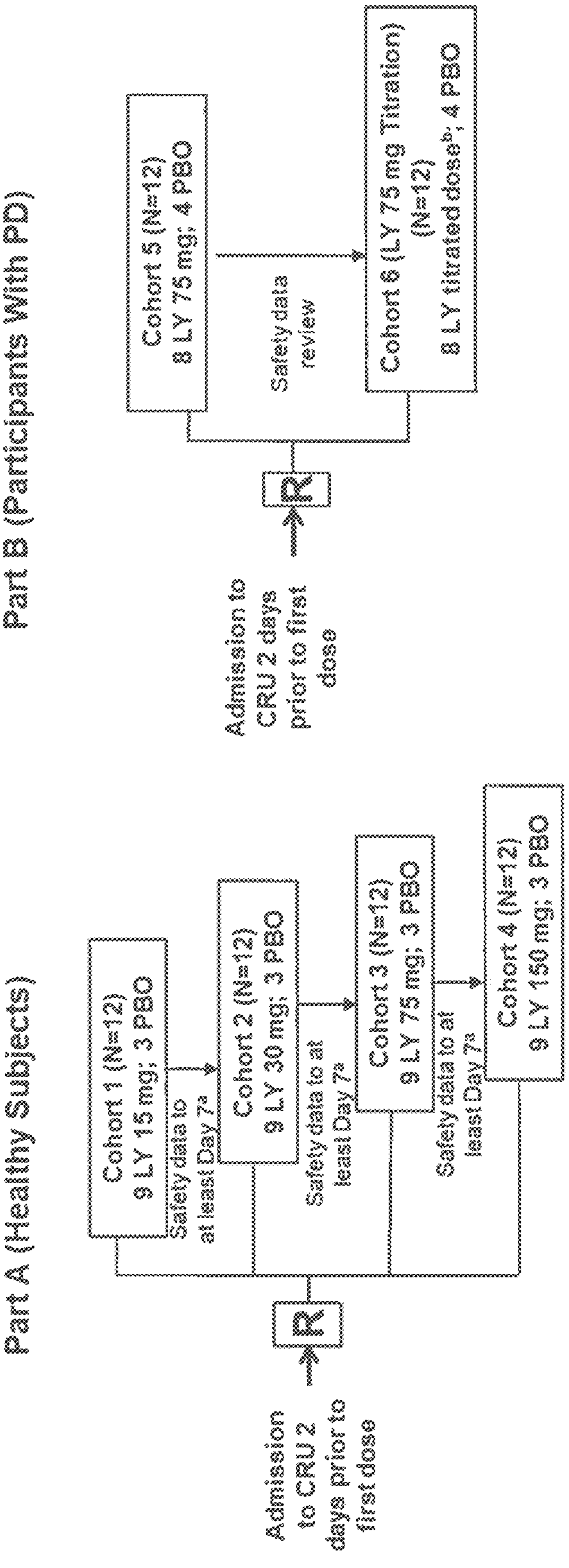

FIG. 3

DOSE REGIMENS FOR USE OF LY3154207 IN THE TREATMENT OF DOPAMINERGIC CNS DISORDERS

CROSS-REFERENCE TO RELATED PATENT APPLICATIONS

The present application is the U.S. National Stage of International Patent Application No. PCT/US2019/066465, filed on Dec. 16, 2019, and published in the English language as WO 2020/131671 on Jun. 25, 2020, which application in turn claims the benefit of priority to U.S. Provisional Patent Application No. 62/781,251, filed on Dec. 18, 2018, and U.S. Provisional Patent Application No. 62/904,048, filed on Sep. 23, 2019. The contents of the foregoing applications are incorporated herein by reference in their entireties.

The present invention provides dosing regimens and methods of using LY3154207, also described as 2-(2,6-dichlorophenyl)-1-[(1S,3R)-3-(hydroxymethyl)-5-(3-hydroxy-3-methylbutyl)-1-methyl-3,4-dihydroisoquinolin-2 (1H)-ylJethanone, and/or pharmaceutical compositions thereof, for treatment of dopaminergic central nervous system disorders. Dopaminergic CNS disorders of the present dosing regimen methods include Parkinson's Disease, Alzheimer's Disease, Lewy body dementia (LBD), Vascular Dementia, Schizophrenia, ADHD, Depression, Autism, chronic musculoskeletal pain, fibromyalgia, cognitive impairment disorders, sleep disorders, excessive daytime sleepiness, narcolepsy, shift work disorder, traumatic brain injury, chronic traumatic encephalopathy, obesity and appetite regulation, mood disorders, lethargy, apathy, and addiction disorders.

Lewy body dementia (LBD) is a progressive brain disorder in which Lewy bodies (abnormal deposits of alpha-synuclein) build up in areas of the brain that regulate behavior, cognition, and movement. LBD is an umbrella term that encompasses two related disorders: Parkinson's Disease Dementia (PDD) and Dementia with Lewy Bodies (DLB). People with LBD can be impacted by a number of symptoms spanning cognition, movement, sleep, mood, behavior, and autonomic dysfunction. Parkinson's disease (PD) is a well-recognized example of a dopaminergic CNS disorder arising from the dysfunction and/or loss of dopaminergic neurons, and a resulting disturbance in normal dopamine signaling. PD is a progressive neurodegenerative movement disorder due to degeneration of dopaminergic neurons in the substantia nigra region of the brain, and Lewy body formation, resulting in reduced dopamine levels in the striatum. PD manifests in tremor along with other motor symptoms (e.g. akinesia and bradykinesia, impaired ability to maintain balance) and non-motor symptoms (e.g. cognitive impairment, sleep disorders, apathy and depression). Executive functioning. visuospatial recognition, attention deficit, and memory and language impairment are the most frequently described cognitive domains affected and are considered to be related to fronto-striatal dopamine insufficiency, with early signs observed in 15% to 20% of subjects at the time of PD diagnosis. Dementia associated with PD is reported in 30% of subjects with PD, 30) and the prevalence increases with disease progression, with a lifetime risk of up to 78%. Standard treatments for PD are acetylcholinesterase inhibitors (AChEI), such as rivastigmine, which offer clinical benefit in a subset of subjects with modest efficacy, but may be associated with motor side effects. Rivastigmine is currently the only approved treatment for mild-to-moderate dementia associated with Parkinson's disease. Therefore, improved treatments of PD and cognitive impairment due to PDD, which are effective, safe, and clinically well-tolerated, remain an unmet medical need.

Dopamine insufficiency has also been observed in subjects with Alzheimer's disease (AD). AD is an age-related neurodegenerative disease that results in the slow decline of cognitive and behavioral functions with the characteristic symptom of memory loss in subjects. Currently available therapies for treatment of AD have modest benefits for the treatment of cognitive impairment, and limited or no benefit for other symptoms in mild to moderate AD patients, such as vigilance, depressive symptoms, day-time alertness, apathy, sleep disruption, memory impairment, executive function (planning/carrying out tasks), and hallucinations. Improved treatments of AD, and associated cognitive impairments, which are effective, safe, and clinically well-tolerated, also remain an unmet medical need.

The dopamine receptor D1 subtype (D1) is the most abundant dopamine receptor in the central nervous system, and plays an important role in multiple CNS functions, including motor activity, reward, and cognitive functions. D1 receptors in pre-frontal cortex important for cognition. D1 receptors mediate acetylcholine release in various brain regions, notably including the hippocampus, and D1 receptors on dendritic spines of cortical neurons are critical for intact working memory, attention and executive functions. For many years the modulation of dopamine signaling in dopaminergic CNS disorders has been attempted with direct D1 receptor agonists, but various D1 agonist agents have achieved very limited success as lack of efficacy, safety, tolerability, including notably unacceptable adverse effects, have limited the utility of such agents. In addition, D1 agonists have bell-shaped dose response curves on cognitive endpoints which complicates and confounds clinical use. Thus, prior attempts to develop clinically useful direct D1 receptor agonists have been largely unsuccessful due to receptor desensitization, poor ADME/PK properties, and dose limiting side effects such as hypotension. Direct acting dopamine therapies are also limited in effectiveness due in part to high dose associated cognition impairment, seizure risk, and tolerance development. Thus, there remains a significant unmet need for safe, effective, and clinically tolerable treatments of Parkinson's disease and other dopaminergic CNS disorders.

LY3154207 is a dopamine D1 receptor Positive Allosteric Modulator (D1 PAM), and represents a potential first-in-class treatment for dementias and other dopaminergic CNS disorders. LY3154207 (CAS Registry No. 1638667-79-4) can be described chemically as 2-(2,6-dichlorophenyl)-1-[(1S,3R)-3-(hydroxymethyl)-5-(3-hydroxy-3-methylbutyl)-1-methyl-3,4-dihydroisoquinolin-2 (1H)-yllethanone, and can be structurally represented as:

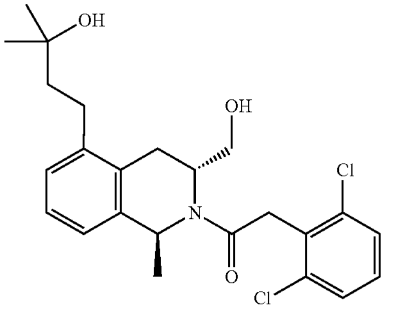 [SMILES: C[C@H]1c2cccc(CCC(C)(C)O)c2C[C@H](CO)N1C(=O)Cc1c(Cl)cccc1Cl]

Useful forms of LY3154207 include a crystalline form (See WO 2017/070068), and a co-crystalline form comprising 2-(2,6-dichlorophenyl)-1-[(1S,3R)-3-(hydroxymethyl)-5-(3-hydroxy-3-methylbutyl)-1-methyl-3,4-dihydroisoquinolin-2 (1H)-ylJethanone and 4-hydroxybenzoic acid (CAS Registry No. 1638669-32-5) (See WO 2014/193781). As a positive allosteric modulator, also called a "potentiator" of the dopamine D1 receptor subtype, LY3154207 is highly selective for D1. LY3154207 shows very weak direct agonism of the DI receptor, and is active only in the presence of dopamine, and believed to be dependent on endogenous tone and subject to normal feedback control. Thus, LY3154207 represents an innovative pharmacological agent and approach to modulating D1 signaling pathways in PD, AD, and other dopaminergic CNS disorders where D1 signaling may be deficient.

LY3154207 has a mechanism of action that differs from other dopaminergic agents such as the direct D1 receptor agonists. LY3154207 binds to a newly discovered allosteric binding site on intracellular loop 2 of the D1 receptor, where it increases the affinity of dopamine for the D1 receptor. A search of the literature to date suggests that no human clinical studies have been published for any D1 PAM agents. Due to the complexity of dopaminergic signaling in normal physiology and clinical disease, and the lack of clinical pharmacological guidance from D1 orthosteric agonists, there remains an important unmet need for clinical dosing regimens of D1 PAMs. In particular there remains an unmet need for clinical dosing regimens of LY3154207 which provide a combined profile of effective, safe, and clinically tolerable pharmacological effects, for use in the treatment of PD, AD, and other dopaminergic CNS disorders.

The present invention provides clinical therapeutic dosing regimens and methods of using LY3154207, and/or pharmaceutical compositions thereof, for use in the treatment of dopaminergic central nervous system disorders. A dopaminergic central nervous system disorder, as defined herein, is one selected from the group consisting of Lewy body dementia (LBD), Parkinson's Disease, Alzheimer's Disease, Vascular Dementia, Schizophrenia, ADHD, Depression, Autism, chronic musculoskeletal pain, fibromyalgia, cognitive impairment disorders, sleep disorders, excessive daytime sleepiness, narcolepsy, shift work disorder, traumatic brain injury, chronic traumatic encephalopathy, obesity and appetite regulation, mood disorders, lethargy, apathy, and addiction disorders. In the dosing regimens of the present invention, and as used herein, LY3154207 is 2-(2,6-dichlorophenyl)-1-[(1S,3R)-3-(hydroxy methyl)-5-(3-hydroxy-3-methylbutyl)-1-methyl-3,4-dihydroisoquinolin-2 (1H)-yllethanone in any form, and includes crystalline and co-crystalline forms thereof, in particular the benzoic acid co-crystalline form, and/or pharmaceutical compositions comprising these agents. The present invention provides a method for use of LY3154207 in the treatment of a dopaminergic central nervous system disorder in a patient, comprising administering to said patient a dose of about 0.5 mg to about 75 mg, up to a maximum total dose of 75 mg per day, of LY3154207, or pharmaceutical composition thereof. The present invention further provides a method for use of LY3154207 in the treatment of a dopaminergic central nervous system disorder in a patient, comprising administering to said patient a dose of about 0.5 mg to about 15 mg, up to a maximum total dose of 15 mg per day, of LY3154207, or pharmaceutical composition thereof.

LY3154207, and a related D1 PAM compound referred to herein as DPTQ, have been studied in primates and/or human phase I studies of healthy volunteers and PD patients, and LY3154207 has entered a phase II clinical study for Parkinson's Disease Dementia (referred to as PRESENCE, NCT03305809). Studies including those described in Example 1 (Phase I Clinical Studies of LY3154207) and Example 2 (Spatial Working Memory in the Adult Rhesus Monkey) have resulted in the concept that LY3154207, when used according to the dosing regimens of the present invention, may induce a surprisingly marked improvement in signs and symptoms of dopaminergic CNS disorders, such as treatment of PD or AD dementia, cognitive enhancement, and/or sleep or appetite regulation. Thus, when used according to the present dosing regimens, LY3154207 provides a means to improve dopamine D1 signaling in a manner that is believed to provide an effective, safe, and clinically tolerable therapeutic regimen, in a variety of dopaminergic CNS disorders.

The dosing regimens of the present invention embody methods which provide surprising and unpredictable advantages. In particular, dopaminergic CNS patients have a need to avoid substantial degrees or risk of insomnia, agitation, and/or undesired cardiovascular effects, such as elevations in pulse and blood pressure, while at the same time needing the benefits of advantageous LY3154207 activities such as alertness, appetite regulation, and/or pro-cognitive or motor control effects. Unexpectedly it has been discovered that clinically useful and desirable effects of LY3154207 in dopaminergic CNS disorders, such as pro-cognitive effects, motor function restoration, appetite reduction, and alertness or wakefulness, can in fact be separated from certain undesirable effects by using the clinical dosing regimens of the present invention.

Thus, the present invention provides certain clinical dosing regimens for the daily administration of LY3154207 such that the dopaminergic central nervous system disorder patient will have relief of the signs and symptoms of their dopaminergic central nervous system disorder while avoiding other D1 PAM effects that would preempt these clinical benefits. In addition, the present invention provides for the chronic daily administration of LY3154207 such that the dopaminergic central nervous system disorder patient will further be able to employ either lower or higher doses of LY3154207 within the regimens of the present invention, such that effective symptomatic relief is achieved for the individual patient while undesirable effects are avoided.

For example, patients may benefit from a dosing regimen of the present invention where the wakefulness and/or appetite reduction effects may be maximized by employing higher doses, up to 75 mg of LY3154207 per day. In another embodiment, the low dose regimen of up to 15 mg of LY3154207 per day provides a means for patients to benefit from cognitive enhancing effects without, at the same time, experiencing excessive wake promotion, agitation, and/or undesirable loss of appetite. Generally, the dosing regimens of the present invention provide the means for patients to benefit from D1 PAM activity, while avoiding certain undesired adverse cardiovascular activities that have been observed clinically, and may represent on-target pharmacology for D1 PAMs as a class. Further, the dosing regimens of the present invention provide a means to treat patients with dopaminergic CNS disorders while at the same time decreasing the risk of drug-drug interactions with Cyp3A4 inhibitors.

Accordingly, the present invention provides dosing regimens for oral daily administration of LY3154207 to a patient having a dopaminergic central nervous system disorder using certain particular doses of LY3154207 which are described in detail below.

In an embodiment, the present invention provides a method for use of LY3154207 in the treatment of a dopaminergic central nervous system disorder in a patient, comprising administering to said patient a dose of about 0.5 mg to about 75 mg, up to a maximum total dose of 75 mg per day, of LY3154207, or pharmaceutical composition thereof.

In an embodiment, the present invention provides a method for use of LY3154207 in the treatment of a dopaminergic central nervous system disorder in a patient, comprising administering to said patient a dose of about 0.5 mg to about 15 mg, up to a maximum total dose of 15 mg per day, of LY3154207, or pharmaceutical composition thereof.

In an embodiment, the present invention provides a method for use of LY3154207 in the treatment of a dopaminergic central nervous system disorder in a patient, comprising administering to said patient a dose per day selected from the group consisting of 0.5 mg, 1 mg, 2 mg, 3 mg, 5 mg, 10 mg, 15 mg, 20 mg, 30 mg, 50 mg, and 75 mg, of LY3154207, or pharmaceutical composition thereof.

In an embodiment, the present invention provides a method for use of LY3154207 in the treatment of a dopaminergic central nervous system disorder in a patient, comprising chronic daily administration to said patient a dose of about 0.5 mg to about 75 mg, up to a maximum total dose of 75 mg per day, of LY3154207, or pharmaceutical composition thereof, wherein the patient is treated for at least 21 consecutive days.

In an embodiment, the present invention provides a method for use of LY3154207 in the treatment of a dopaminergic central nervous system disorder in a patient, comprising chronic daily administration to said patient a dose of about 0.5 mg to about 15 mg, up to a maximum total dose of 15 mg per day, of LY3154207, or pharmaceutical composition thereof, wherein the patient is treated for at least 21 consecutive days.

In an embodiment, the present invention provides a method for use of LY3154207 in the treatment of a dopaminergic central nervous system disorder in a patient, comprising chronic daily administration to said patient a dose per day selected from the group consisting of 0.5 mg, 1 mg, 2 mg, 3 mg, 5 mg, 10 mg, 15 mg, 20 mg, 30 mg, 50 mg, and 75 mg, of LY3154207, or pharmaceutical composition thereof, wherein the patient is treated for at least 21 consecutive days.

In an embodiment, the present invention provides a method for use of LY3154207 in the treatment of a dopaminergic central nervous system disorder in a patient, comprising administering to said patient a dose of about 0.5 mg to about 75 mg, up to a maximum total dose of 75 mg per day, of LY3154207, or pharmaceutical composition thereof, wherein said dopaminergic central nervous system disorder is selected from the group consisting of Lewy body dementia (LBD), Parkinson's Disease, Alzheimer's Disease, Vascular Dementia, Schizophrenia, ADHD, Depression, Autism, chronic musculoskeletal pain, fibromyalgia, cognitive impairment disorders, excessive daytime sleepiness, narcolepsy, shift work disorder, traumatic brain injury, chronic traumatic encephalopathy, obesity and appetite regulation, mood disorders, lethargy, apathy, and addiction disorders.

In an embodiment, the present invention provides a method for use of LY3154207 in the treatment of a dopaminergic central nervous system disorder in a patient, comprising administering to said patient a dose of about 0.5 mg to about 15 mg, up to a maximum total dose of 15 mg per day, of LY3154207, or pharmaceutical composition thereof, wherein said dopaminergic central nervous system disorder is selected from the group consisting of Lewy body dementia (LBD), Parkinson's Disease, Alzheimer's Disease, Vascular Dementia, Schizophrenia, ADHD, Depression, Autism, chronic musculoskeletal pain, fibromyalgia, cognitive impairment disorders, excessive daytime sleepiness, narcolepsy, shift work disorder, traumatic brain injury, chronic traumatic encephalopathy, obesity and appetite regulation, mood disorders, lethargy, apathy, and addiction disorders.

In an embodiment, the present invention provides a method for use of LY3154207 in the treatment of a dopaminergic central nervous system disorder in a patient, comprising chronic daily administration to said patient a dose of about 0.5 mg to about 75 mg, up to a maximum total dose of 75 mg per day, of LY3154207, or pharmaceutical composition thereof, wherein said dopaminergic central nervous system disorder is selected from the group consisting of Lewy body dementia (LBD), Parkinson's Disease, Alzheimer's Disease, Vascular Dementia, Schizophrenia, ADHD, Depression, Autism, chronic musculoskeletal pain, fibromyalgia, cognitive impairment disorders, excessive daytime sleepiness, narcolepsy, shift work disorder, traumatic brain injury, chronic traumatic encephalopathy, obesity and appetite regulation, mood disorders, lethargy, apathy, and addiction disorders, wherein the patient is treated for at least 21 consecutive days.

In an embodiment, the present invention provides a method for use of LY3154207 in the treatment of a dopaminergic central nervous system disorder in a patient, comprising administering to said patient a dose of about 0.5 mg to about 15 mg, up to a maximum total dose of 15 mg per day, of LY3154207, or pharmaceutical composition thereof, wherein said dopaminergic central nervous system disorder is selected from the group consisting of Lewy body dementia (LBD), Parkinson's Disease, Alzheimer's Disease, Vascular Dementia, Schizophrenia, ADHD, Depression, Autism, chronic musculoskeletal pain, fibromyalgia, cognitive impairment disorders, excessive daytime sleepiness, narcolepsy, shift work disorder, traumatic brain injury, chronic traumatic encephalopathy, obesity and appetite regulation, mood disorders, lethargy, apathy, and addiction disorders, wherein the patient is treated for at least 21 consecutive days.

In an embodiment, the present invention provides a method for use of LY3154207 in the treatment of a dopaminergic central nervous system disorder in a patient, comprising administering to said patient a dose of 0.5 mg per day of LY3154207, or pharmaceutical composition thereof.

In an embodiment, the present invention provides a method for use of LY3154207 in the treatment of a dopaminergic central nervous system disorder in a patient, comprising administering to said patient a dose of 1 mg per day of LY3154207, or pharmaceutical composition thereof.

In an embodiment, the present invention provides a method for use of LY3154207 in the treatment of a dopaminergic central nervous system disorder in a patient, comprising administering to said patient a dose of 2 mg per day of LY3154207, or pharmaceutical composition thereof.

In an embodiment, the present invention provides a method for use of LY3154207 in the treatment of a dopaminergic central nervous system disorder in a patient, comprising administering to said patient a dose of 3 mg per day of LY3154207, or pharmaceutical composition thereof.

In an embodiment, the present invention provides a method for use of LY3154207 in the treatment of a dopaminergic central nervous system disorder in a patient, comprising administering to said patient a dose of 5 mg per day of LY3154207, or pharmaceutical composition thereof.

In an embodiment, the present invention provides a method for use of LY3154207 in the treatment of a dopaminergic central nervous system disorder in a patient, comprising administering to said patient a dose of 10 mg per day of LY3154207, or pharmaceutical composition thereof.

In an embodiment, the present invention provides a method for use of LY3154207 in the treatment of a dopaminergic central nervous system disorder in a patient, comprising administering to said patient a dose of 15 mg per day of LY3154207, or pharmaceutical composition thereof.

In an embodiment, the present invention provides a method for use of LY3154207 in the treatment of a dopaminergic central nervous system disorder in a patient, comprising administering to said patient a dose of 20 mg per day of LY3154207, or pharmaceutical composition thereof.

In an embodiment, the present invention provides a method for use of LY3154207 in the treatment of a dopaminergic central nervous system disorder in a patient, comprising administering to said patient a dose of 30 mg per day of LY3154207, or pharmaceutical composition thereof.

In an embodiment, the present invention provides a method for use of LY3154207 in the treatment of a dopaminergic central nervous system disorder in a patient, comprising administering to said patient a dose of 50 mg per day of LY3154207, or pharmaceutical composition thereof.

In an embodiment, the present invention provides a method of claim 1 for use of LY3154207 in the treatment of a dopaminergic central nervous system disorder in a patient, comprising administering to said patient a dose of 75 mg per day of LY3154207, or pharmaceutical compos In an embodiment, the present invention provides a method for use of LY3154207 in the treatment of Parkinson's Disease in a patient, comprising administering to said patient a dose of about 0.5 mg to about 75 mg, up to a maximum total dose of 75 mg per day, of LY3154207, or pharmaceutical composition thereof.

In an embodiment, the present invention provides a method for use of LY3154207 in the treatment of Parkinson's Disease in a patient, comprising administering to said patient a dose of about 0.5 mg to about 15 mg, up to a maximum total dose of 15 mg per day, of LY3154207, or pharmaceutical composition thereof.

In an embodiment, the present invention provides a method for use of LY3154207 in the treatment of Parkinson's Disease in a patient, comprising administering to said patient a dose per day selected from the group consisting of 0.5 mg, 1 mg, 2 mg, 3 mg, 5 mg, 10 mg, 15 mg, 20 mg, 30 mg, 50 mg, and 75 mg, of LY3154207, or pharmaceutical composition thereof.

In an embodiment, the present invention provides a method for use of LY3154207 in the treatment of Parkinson's Disease in a patient, comprising administering to said patient a dose of about 0.5 mg to about 75 mg, up to a maximum total dose of 75 mg per day, of LY3154207, or pharmaceutical composition thereof, wherein the patient meets the revised MDS criteria for PD and mild-to-moderate dementia as defined by a decline in cognitive function with an MoCA score between 10 and 23.

In an embodiment, the present invention provides a method for use of LY3154207 in the treatment of Parkinson's Disease in a patient, comprising chronic daily administration to said patient a dose of about 0.5 mg to about 75 mg, up to a maximum total dose of 75 mg per day, of LY3154207, or pharmaceutical composition thereof, wherein the patient is treated for at least 21 consecutive days.

In an embodiment, the present invention provides a method for use of LY3154207 in the treatment of Alzheimer's Disease in a patient, comprising administering to said patient a dose of about 0.5 mg to about 75 mg, up to a maximum total dose of 75 mg per day, of LY3154207, or pharmaceutical composition thereof.

In an embodiment, the present invention provides a method for use of LY3154207 in the treatment of Alzheimer's Disease in a patient, comprising administering to said patient a dose of about 0.5 mg to about 15 mg, up to a maximum total dose of 15 mg per day, of LY3154207, or pharmaceutical composition thereof.

In an embodiment, the present invention provides a method for use of LY3154207 in the treatment of Alzheimer's Disease in a patient, comprising administering to said patient a dose per day selected from the group consisting of 0.5 mg, 1 mg, 2 mg, 3 mg, 5 mg, 10 mg, 15 mg, 20 mg, 30 mg, 50 mg, and 75 mg, of LY3154207, or pharmaceutical composition thereof.

In an embodiment, the present invention provides a method for use of LY3154207 in the treatment of Alzheimer's Disease in a patient, comprising chronic daily administration to said patient a dose of about 0.5 mg to about 75 mg, up to a maximum total dose of 75 mg per day, of LY3154207, or pharmaceutical composition thereof, wherein the patient is treated for at least 21 consecutive days.

In an embodiment, the present invention provides a method for use of LY3154207 for inducing weight loss in a patient, comprising administering to said patient a dose of about 0.5 mg to about 75 mg, up to a maximum total dose of 75 mg per day, of LY3154207, or pharmaceutical composition thereof.

In an embodiment, the present invention provides a method for use of LY3154207 for inducing weight loss in a patient, comprising administering to said patient a dose of about 0.5 mg to about 15 mg, up to a maximum total dose of 15 mg per day, of LY3154207, or pharmaceutical composition thereof.

In an embodiment, the present invention provides a method for use of LY3154207 for inducing weight loss in a patient, comprising administering to said patient a dose per day selected from the group consisting of 0.5 mg, 1 mg, 2 mg, 3 mg, 5 mg, 10 mg, 15 mg, 20 mg, 30 mg, 50 mg, and 75 mg, of LY3154207, or pharmaceutical composition thereof.

In an embodiment, the present invention provides a method for use of LY3154207 for inducing weight loss in a patient, comprising chronic daily administration to said patient a dose of about 0.5 mg to about 75 mg, up to a maximum total dose of 75 mg per day, of LY3154207, or pharmaceutical composition thereof, wherein the patient is treated for at least 21 consecutive days.

In an embodiment, the present invention provides a method for use of LY3151944 in the treatment of a dopaminergic central nervous system disorder in a patient, comprising administering to said patient a dose of about 0.5 mg to about 75 mg, up to a maximum total dose of 75 mg per day, of LY3151944, or pharmaceutical composition thereof.

In an embodiment, the present invention provides a method for use of LY3151944 in the treatment of a dopaminergic central nervous system disorder in a patient, comprising administering to said patient a dose of about 0.5 mg to about 15 mg, up to a maximum total dose of 15 mg per day, of LY3151944, or pharmaceutical composition thereof.

In an embodiment, the present invention provides LY3154207, or pharmaceutical composition thereof, for use in the treatment of a dopaminergic central nervous system disorder in a patient, comprising administering to said patient one or more doses of about 0.5 mg to about 75 mg per day, up to a maximum total dose of 75 mg per day, of LY3154207, or pharmaceutical composition thereof.

In a preferred embodiment, the present invention provides LY3154207, or pharmaceutical composition thereof, for use in the treatment of a dopaminergic central nervous system disorder in a patient, comprising administering to said patient one or more doses of about 0.5 mg to about 15 mg per day, up to a maximum total dose of 15 mg per day, of LY3154207, or pharmaceutical composition thereof.

In a preferred embodiment, the present invention provides LY3154207, or pharmaceutical composition thereof, for use in the treatment of a dopaminergic central nervous system disorder in a patient, comprising administering to said patient a dose per day selected from the group consisting of 0.5 mg, 1 mg, 2 mg, 3 mg, 5 mg, 10 mg, 15 mg, 20 mg, 30 mg, 50 mg, and 75 mg, of LY3154207, or pharmaceutical composition thereof.

In a preferred embodiment, the present invention provides LY3154207, or pharmaceutical composition thereof, for use in the treatment of a dopaminergic central nervous system disorder in a patient, comprising chronically administering to said patient one or more doses of about 0.5 mg to about 75 mg per day, up to a maximum total dose of 75 mg per day, of LY3154207, or pharmaceutical composition thereof, wherein the patient is treated for at least 21 consecutive days.

In a preferred embodiment, the present invention provides LY3154207, or pharmaceutical composition thereof, for use according to embodiments above, comprising chronically administering to said patient one or more doses of about 0.5 mg to about 15 mg per day, up to a maximum total dose of 15 mg per day, of LY3154207, or pharmaceutical composition thereof.

In a preferred embodiment, the present invention provides LY3154207, or pharmaceutical composition thereof, for use according to embodiments above, comprising chronically administering to said patient a dose per day selected from the group consisting of 0.5 mg, 1 mg, 2 mg, 3 mg, 5 mg, 10 mg, 15 mg, 20 mg, 30 mg, 50 mg, and 75 mg, of LY3154207, or pharmaceutical composition thereof.

In a preferred embodiment, the present invention provides LY3154207, or pharmaceutical composition thereof, for use according to embodiments above, wherein said dopaminergic central nervous system disorder is selected from the group consisting of Lewy body dementia (LBD), Parkinson's Disease, Alzheimer's Disease, Vascular Dementia, Schizophrenia, ADHD, Depression, Autism, chronic musculoskeletal pain, fibromyalgia, cognitive impairment disorders, excessive daytime sleepiness, narcolepsy, shift work disorder, traumatic brain injury, chronic traumatic encephalopathy, obesity and appetite regulation, mood disorders, lethargy, apathy, and addiction disorders.

In a preferred embodiment, the present invention provides LY3154207, or pharmaceutical composition thereof, for use according to embodiments above, comprising administering to said patient a dose of 0.5 mg per day of LY3154207, or pharmaceutical composition thereof.

In a preferred embodiment, the present invention provides LY3154207, or pharmaceutical composition thereof, for use according to embodiments above, comprising administering to said patient a dose of 1 mg per day of LY3154207, or pharmaceutical composition thereof.

In a preferred embodiment, the present invention provides LY3154207, or pharmaceutical composition thereof, for use according to embodiments above, comprising administering to said patient a dose of 2 mg per day of LY3154207, or pharmaceutical composition thereof.

In a preferred embodiment, the present invention provides LY3154207, or pharmaceutical composition thereof, for use according to embodiments above, comprising administering to said patient a dose of 3 mg per day of LY3154207, or pharmaceutical composition thereof.

In a preferred embodiment, the present invention provides LY3154207, or pharmaceutical composition thereof, for use according to embodiments above, comprising administering to said patient a dose of 5 mg per day of LY3154207, or pharmaceutical composition thereof.

In a preferred embodiment, the present invention provides LY3154207, or pharmaceutical composition thereof, for use according to embodiments above, comprising administering to said patient a dose of 10 mg per day of LY3154207, or pharmaceutical composition thereof.

In a preferred embodiment, the present invention provides LY3154207, or pharmaceutical composition thereof, for use according to embodiments above, comprising administering to said patient a dose of 15 mg per day of LY3154207, or pharmaceutical composition thereof.

In a preferred embodiment, the present invention provides LY3154207, or pharmaceutical composition thereof, for use according to embodiments above, comprising administering to said patient a dose of 20 mg per day of LY3154207, or pharmaceutical composition thereof.

In a preferred embodiment, the present invention provides LY3154207, or pharmaceutical composition thereof, for use according to embodiments above, comprising administering to said patient a dose of 30 mg per day of LY3154207, or pharmaceutical composition thereof.

In a preferred embodiment, the present invention provides LY3154207, or pharmaceutical composition thereof, for use according to embodiments above, comprising administering to said patient a dose of 50 mg per day of LY3154207, or pharmaceutical composition thereof.

In a preferred embodiment, the present invention provides LY3154207, or pharmaceutical composition thereof, for use according to embodiments above, comprising administering to said patient a dose of 75 mg per day of LY3154207, or pharmaceutical composition thereof.

In a preferred embodiment, the present invention provides LY3154207, or pharmaceutical composition thereof, for use according to embodiments above, wherein said dopaminergic central nervous system disorder is Parkinson's Disease.

In a preferred embodiment, the present invention provides LY3154207, or pharmaceutical composition thereof, for use according to embodiments above, wherein the patient meets the revised MDS criteria for PD and mild-to-moderate dementia as defined by a decline in cognitive function with an MoCA score between 10 and 23.

In a preferred embodiment, the present invention provides LY3154207, or pharmaceutical composition thereof, for use according to embodiments above, wherein said dopaminergic central nervous system disorder is Alzheimer's Disease.

In a preferred embodiment, the present invention provides LY3154207, or pharmaceutical composition thereof, for use according to embodiments above, wherein said dopaminergic central nervous system disorder is obesity.

In an embodiment, the present invention provides LY3154207, or pharmaceutical composition thereof, for use in the treatment of a dopaminergic central nervous system disorder in a patient, comprising administering to said patient a dose of about 0.5 mg to about 15 mg, up to a maximum total dose of 15 mg per day, of LY3154207, or pharmaceutical composition thereof.

In an embodiment, the present invention provides LY3154207, or pharmaceutical composition thereof, for use in the treatment of a dopaminergic central nervous system disorder in a patient, comprising administering to said patient a dose per day selected from the group consisting of 0.5 mg, 1 mg, 2 mg, 3 mg, 5 mg, 10 mg, 15 mg, 20 mg, 30 mg, 50 mg, and 75 mg, of LY3154207, or pharmaceutical composition thereof.

In an embodiment, the present invention provides LY3154207, or pharmaceutical composition thereof, for use in the treatment of a dopaminergic central nervous system disorder in a patient, comprising chronic daily administration to said patient a dose of about 0.5 mg to about 75 mg, up to a maximum total dose of 75 mg per day, of LY3154207, or pharmaceutical composition thereof, wherein the patient is treated for at least 21 consecutive days.

In an embodiment, the present invention provides LY3154207, or pharmaceutical composition thereof, for use in the treatment of a dopaminergic central nervous system disorder in a patient, comprising chronic daily administration to said patient a dose of about 0.5 mg to about 15 mg, up to a maximum total dose of 15 mg per day, of LY3154207, or pharmaceutical composition thereof, wherein the patient is treated for at least 21 consecutive days.

In an embodiment, the present invention provides LY3154207, or pharmaceutical composition thereof, for use in the treatment of a dopaminergic central nervous system disorder in a patient, comprising chronic daily administration to said patient a dose per day selected from the group consisting of 0.5 mg, 1 mg, 2 mg, 3 mg, 5 mg, 10 mg, 15 mg, 20 mg, 30 mg, 50 mg, and 75 mg, of LY3154207, or pharmaceutical composition thereof, wherein the patient is treated for at least 21 consecutive days.

In an embodiment, the present invention provides LY3154207, or pharmaceutical composition thereof, for use in the treatment of a dopaminergic central nervous system disorder in a patient, comprising administering to said patient a dose of about 0.5 mg to about 75 mg, up to a maximum total dose of 75 mg per day, of LY3154207, or pharmaceutical composition thereof, wherein said dopaminergic central nervous system disorder is selected from the group consisting of Lewy body dementia (LBD), Parkinson's Disease, Alzheimer's Disease, Vascular Dementia, Schizophrenia, ADHD, Depression, Autism, chronic musculoskeletal pain, fibromyalgia, cognitive impairment disorders, excessive daytime sleepiness, narcolepsy, shift work disorder, traumatic brain injury, chronic traumatic encephalopathy, obesity and appetite regulation, mood disorders, lethargy, apathy, and addiction disorders.

In an embodiment, the present invention provides LY3154207, or pharmaceutical composition thereof, for use in the treatment of a dopaminergic central nervous system disorder in a patient, comprising administering to said patient a dose of about 0.5 mg to about 15 mg, up to a maximum total dose of 15 mg per day, of LY3154207, or pharmaceutical composition thereof, wherein said dopaminergic central nervous system disorder is selected from the group consisting of Lewy body dementia (LBD), Parkinson's Disease, Alzheimer's Disease, Vascular Dementia, Schizophrenia, ADHD, Depression, Autism, chronic musculoskeletal pain, fibromyalgia, cognitive impairment disorders, excessive daytime sleepiness, narcolepsy, shift work disorder, traumatic brain injury, chronic traumatic encephalopathy, obesity and appetite regulation, mood disorders, lethargy, apathy, and addiction disorders.

In an embodiment, the present invention provides LY3154207, or pharmaceutical composition thereof, for use in the treatment of a dopaminergic central nervous system disorder in a patient, comprising chronic daily administration to said patient a dose of about 0.5 mg to about 75 mg, up to a maximum total dose of 75 mg per day, of LY3154207, or pharmaceutical composition thereof, wherein said dopaminergic central nervous system disorder is selected from the group consisting of Lewy body dementia (LBD), Parkinson's Disease, Alzheimer's Disease, Vascular Dementia, Schizophrenia, ADHD, Depression, Autism, chronic musculoskeletal pain, fibromyalgia, cognitive impairment disorders, excessive daytime sleepiness, narcolepsy, shift work disorder, traumatic brain injury, chronic traumatic encephalopathy, obesity and appetite regulation, mood disorders, lethargy, apathy, and addiction disorders, wherein the patient is treated for at least 21 consecutive days. In an embodiment, the present invention provides LY3154207, or pharmaceutical composition thereof, for use in the treatment of a dopaminergic central nervous system disorder in a patient, comprising administering to said patient a dose of about 0.5 mg to about 15 mg, up to a maximum total dose of 15 mg per day, of LY3154207, or pharmaceutical composition thereof, wherein said dopaminergic central nervous system disorder is selected from the group consisting of Lewy body dementia (LBD), Parkinson's Disease, Alzheimer's Disease, Vascular Dementia, Schizophrenia, ADHD, Depression, Autism, chronic musculoskeletal pain, fibromyalgia, cognitive impairment disorders, excessive daytime sleepiness, narcolepsy, shift work disorder, traumatic brain injury, chronic traumatic encephalopathy, obesity and appetite regulation, mood disorders, lethargy, apathy, and addiction disorders, wherein the patient is treated for at least 21 consecutive days.

In an embodiment, the present invention provides LY3154207, or pharmaceutical composition thereof, for use in the treatment of a dopaminergic central nervous system disorder in a patient, comprising administering to said patient a dose of 0.5 mg per day of LY3154207, or pharmaceutical composition thereof.

In an embodiment, the present invention provides LY3154207, or pharmaceutical composition thereof, for use in the treatment of a dopaminergic central nervous system disorder in a patient, comprising administering to said patient a dose of 1 mg per day of LY3154207, or pharmaceutical composition thereof.

In an embodiment, the present invention provides LY3154207, or pharmaceutical composition thereof, for use in the treatment of a dopaminergic central nervous system disorder in a patient, comprising administering to said patient a dose of 2 mg per day of LY3154207, or pharmaceutical composition thereof.

In an embodiment, the present invention provides LY3154207, or pharmaceutical composition thereof, for use in the treatment of a dopaminergic central nervous system disorder in a patient, comprising administering to said patient a dose of 3 mg per day of LY3154207, or pharmaceutical composition thereof.

In an embodiment, the present invention provides LY3154207, or pharmaceutical composition thereof, for use in the treatment of a dopaminergic central nervous system disorder in a patient, comprising administering to said patient a dose of 5 mg per day of LY3154207, or pharmaceutical composition thereof.

In an embodiment, the present invention provides LY3154207, or pharmaceutical composition thereof, for use in the treatment of a dopaminergic central nervous system disorder in a patient, comprising administering to said patient a dose of 10 mg per day of LY3154207, or pharmaceutical composition thereof.

In an embodiment, the present invention provides LY3154207, or pharmaceutical composition thereof, for use in the treatment of a dopaminergic central nervous system disorder in a patient, comprising administering to said patient a dose of 15 mg per day of LY3154207, or pharmaceutical composition thereof.

In an embodiment, the present invention provides LY3154207, or pharmaceutical composition thereof, for use in the treatment of a dopaminergic central nervous system disorder in a patient, comprising administering to said patient a dose of 20 mg per day of LY3154207, or pharmaceutical composition thereof.

In an embodiment, the present invention provides LY3154207, or pharmaceutical composition thereof, for use in the treatment of a dopaminergic central nervous system disorder in a patient, comprising administering to said patient a dose of 30 mg per day of LY3154207, or pharmaceutical composition thereof.

In an embodiment, the present invention provides LY3154207, or pharmaceutical composition thereof, for use in the treatment of a dopaminergic central nervous system disorder in a patient, comprising administering to said patient a dose of 50 mg per day of LY3154207, or pharmaceutical composition thereof.

In an embodiment, the present invention provides LY3154207, or pharmaceutical composition thereof, for use in the treatment of a dopaminergic central nervous system disorder in a patient, comprising administering to said patient a dose of 75 mg per day of LY3154207, or pharmaceutical composition thereof.

In an embodiment, the present invention provides LY3154207, or pharmaceutical composition thereof, for use in the treatment of Parkinson's Disease in a patient, comprising administering to said patient a dose of about 0.5 mg to about 75 mg, up to a maximum total dose of 75 mg per day, of LY3154207, or pharmaceutical composition thereof.

In an embodiment, the present invention provides LY3154207, or pharmaceutical composition thereof, for use in the treatment of Parkinson's Disease in a patient, comprising administering to said patient a dose of about 0.5 mg to about 15 mg, up to a maximum total dose of 15 mg per day, of LY3154207, or pharmaceutical composition thereof.

In an embodiment, the present invention provides LY3154207, or pharmaceutical composition thereof, for use in the treatment of Parkinson's Disease in a patient, comprising administering to said patient a dose per day selected from the group consisting of 0.5 mg, 1 mg, 2 mg, 3 mg, 5 mg, 10 mg, 15 mg, 20 mg, 30 mg, 50 mg, and 75 mg, of LY3154207, or pharmaceutical composition thereof.

In an embodiment, the present invention provides LY3154207, or pharmaceutical composition thereof, for use in the treatment of Parkinson's Disease in a patient, comprising administering to said patient a dose of about 0.5 mg to about 75 mg, up to a maximum total dose of 75 mg per day, of LY3154207, or pharmaceutical composition thereof, wherein the patient meets the revised MDS criteria for PD and mild-to-moderate dementia as defined by a decline in cognitive function with an MoCA score between 10 and 23.

In an embodiment, the present invention provides LY3154207, or pharmaceutical composition thereof, for use in the treatment of Parkinson's Disease in a patient, comprising chronic daily administration to said patient a dose of about 0.5 mg to about 75 mg, up to a maximum total dose of 75 mg per day, of LY3154207, or pharmaceutical composition thereof, wherein the patient is treated for at least 21 consecutive days.

In an embodiment, the present invention provides LY3154207, or pharmaceutical composition thereof, for use in the treatment of Alzheimer's Disease in a patient, comprising administering to said patient a dose of about 0.5 mg to about 75 mg, up to a maximum total dose of 75 mg per day, of LY3154207, or pharmaceutical composition thereof.

In an embodiment, the present invention provides LY3154207, or pharmaceutical composition thereof, for use in the treatment of Alzheimer's Disease in a patient, comprising administering to said patient a dose of about 0.5 mg to about 15 mg, up to a maximum total dose of 15 mg per day, of LY3154207, or pharmaceutical composition thereof.

In an embodiment, the present invention provides LY3154207, or pharmaceutical composition thereof, for use in the treatment of Alzheimer's Disease in a patient, comprising administering to said patient a dose per day selected from the group consisting of 0.5 mg, 1 mg, 2 mg, 3 mg, 5 mg, 10 mg, 15 mg, 20 mg, 30 mg, 50 mg, and 75 mg, of LY3154207, or pharmaceutical composition thereof.

In an embodiment, the present invention provides LY3154207, or pharmaceutical composition thereof, for use in the treatment of Alzheimer's Disease in a patient, comprising chronic daily administration to said patient a dose of about 0.5 mg to about 75 mg, up to a maximum total dose of 75 mg per day, of LY3154207, or pharmaceutical composition thereof, wherein the patient is treated for at least 21 consecutive days.

In an embodiment, the present invention provides LY3154207, or pharmaceutical composition thereof, for use in inducing weight loss in a patient, comprising administering to said patient a dose of about 0.5 mg to about 75 mg, up to a maximum total dose of 75 mg per day, of LY3154207, or pharmaceutical composition thereof.

In an embodiment, the present invention provides LY3154207, or pharmaceutical composition thereof, for use in inducing weight loss in a patient, comprising administering to said patient a dose of about 0.5 mg to about 15 mg, up to a maximum total dose of 15 mg per day, of LY3154207, or pharmaceutical composition thereof.

In an embodiment, the present invention provides LY3154207, or pharmaceutical composition thereof, for use in inducing weight loss in a patient, comprising administering to said patient a dose per day selected from the group consisting of 0.5 mg, 1 mg, 2 mg, 3 mg, 5 mg, 10 mg, 15 mg, 20 mg, 30 mg, 50 mg, and 75 mg, of LY3154207, or pharmaceutical composition thereof.

In an embodiment, the present invention provides LY3154207, or pharmaceutical composition thereof, for use in inducing weight loss in a patient, comprising chronic daily administration to said patient a dose of about 0.5 mg to about 75 mg, up to a maximum total dose of 75 mg per day, of LY3154207, or pharmaceutical composition thereof, wherein the patient is treated for at least 21 consecutive days.

In an embodiment, the present invention provides LY3154207, or pharmaceutical composition thereof, for the manufacture of a medicament for use in the treatment of a dopaminergic central nervous system disorder in a patient, comprising administering to said patient a dose of about 0.5 mg to about 75 mg, up to a maximum total dose of 75 mg per day, of LY3154207, or pharmaceutical composition thereof.

In an embodiment, the present invention provides LY3154207, or pharmaceutical composition thereof, for the manufacture of a medicament for use in the treatment of a dopaminergic central nervous system disorder in a patient, comprising administering to said patient a dose of about 0.5 mg to about 15 mg, up to a maximum total dose of 15 mg per day, of LY3154207, or pharmaceutical composition thereof.

In an embodiment, the present invention provides LY3154207, or pharmaceutical composition thereof, for the manufacture of a medicament for use in the treatment of a dopaminergic central nervous system disorder in a patient, comprising administering to said patient a dose per day selected from the group consisting of 0.5 mg, 1 mg, 2 mg, 3 mg, 5 mg, 10 mg, 15 mg, 20 mg, 30 mg, 50 mg, and 75 mg, of LY3154207, or pharmaceutical composition thereof.

In an embodiment, the present invention provides LY3154207, or pharmaceutical composition thereof, for the manufacture of a medicament for use in the treatment of a dopaminergic central nervous system disorder in a patient, comprising chronic daily administration to said patient a dose of about 0.5 mg to about 75 mg, up to a maximum total dose of 75 mg per day, of LY3154207, or pharmaceutical composition thereof, wherein the patient is treated for at least 21 consecutive days.

In an embodiment, the present invention provides LY3154207, or pharmaceutical composition thereof, for the manufacture of a medicament for use in the treatment of a dopaminergic central nervous system disorder in a patient, comprising chronic daily administration to said patient a dose of about 0.5 mg to about 15 mg, up to a maximum total dose of 15 mg per day, of LY3154207, or pharmaceutical composition thereof, wherein the patient is treated for at least 21 consecutive days.

In an embodiment, the present invention provides LY3154207, or pharmaceutical composition thereof, for the manufacture of a medicament for use in the treatment of a dopaminergic central nervous system disorder in a patient, comprising chronic daily administration to said patient a dose per day selected from the group consisting of 0.5 mg, 1 mg, 2 mg, 3 mg, 5 mg, 10 mg, 15 mg, 20 mg, 30 mg, 50 mg, and 75 mg, of LY3154207, or pharmaceutical composition thereof, wherein the patient is treated for at least 21 consecutive days.

In an embodiment, the present invention provides LY3154207, or pharmaceutical composition thereof, for the manufacture of a medicament for use in the treatment of a dopaminergic central nervous system disorder in a patient, comprising administering to said patient a dose of about 0.5 mg to about 75 mg, up to a maximum total dose of 75 mg per day, of LY3154207, or pharmaceutical composition thereof, wherein said dopaminergic central nervous system disorder is selected from the group consisting of Lewy body dementia (LBD), Parkinson's Disease, Alzheimer's Disease, Vascular Dementia, Schizophrenia, ADHD, Depression, Autism, chronic musculoskeletal pain, fibromyalgia, cognitive impairment disorders, excessive daytime sleepiness, narcolepsy, shift work disorder, traumatic brain injury, chronic traumatic encephalopathy, obesity and appetite regulation, mood disorders, lethargy, apathy, and addiction disorders.

In an embodiment, the present invention provides LY3154207, or pharmaceutical composition thereof, for the manufacture of a medicament for use in the treatment of a dopaminergic central nervous system disorder in a patient, comprising administering to said patient a dose of about 0.5 mg to about 15 mg, up to a maximum total dose of 15 mg per day, of LY3154207, or pharmaceutical composition thereof, wherein said dopaminergic central nervous system disorder is selected from the group consisting of Lewy body dementia (LBD), Parkinson's Disease, Alzheimer's Disease, Vascular Dementia, Schizophrenia, ADHD, Depression, Autism, chronic musculoskeletal pain, fibromyalgia, cognitive impairment disorders, excessive daytime sleepiness, narcolepsy, shift work disorder, traumatic brain injury, chronic traumatic encephalopathy, obesity and appetite regulation, mood disorders, lethargy, apathy, and addiction disorders.

In an embodiment, the present invention provides LY3154207, or pharmaceutical composition thereof, for the manufacture of a medicament for use in the treatment of a dopaminergic central nervous system disorder in a patient, comprising chronic daily administration to said patient a dose of about 0.5 mg to about 75 mg, up to a maximum total dose of 75 mg per day, of LY3154207, or pharmaceutical composition thereof, wherein said dopaminergic central nervous system disorder is selected from the group consisting of Lewy body dementia (LBD), Parkinson's Disease, Alzheimer's Disease, Vascular Dementia, Schizophrenia, ADHD, Depression, Autism, chronic musculoskeletal pain, fibromyalgia, cognitive impairment disorders, excessive daytime sleepiness, narcolepsy, shift work disorder, traumatic brain injury, chronic traumatic encephalopathy, obesity and appetite regulation, mood disorders, lethargy, apathy, and addiction disorders, wherein the patient is treated for at least 21 consecutive days.

In an embodiment, the present invention provides LY3154207, or pharmaceutical composition thereof, for the manufacture of a medicament for use in the treatment of a dopaminergic central nervous system disorder in a patient, comprising administering to said patient a dose of about 0.5 mg to about 15 mg, up to a maximum total dose of 15 mg per day, of LY3154207, or pharmaceutical composition thereof, wherein said dopaminergic central nervous system disorder is selected from the group consisting of Lewy body dementia (LBD), Parkinson's Disease, Alzheimer's Disease, Vascular Dementia, Schizophrenia, ADHD, Depression, Autism, chronic musculoskeletal pain, fibromyalgia, cognitive impairment disorders, excessive daytime sleepiness, narcolepsy, shift work disorder, traumatic brain injury, chronic traumatic encephalopathy, obesity and appetite regulation, mood disorders, lethargy, apathy, and addiction disorders, wherein the patient is treated for at least 21 consecutive days.

In an embodiment, the present invention provides LY3154207, or pharmaceutical composition thereof, for the manufacture of a medicament for use in the treatment of a dopaminergic central nervous system disorder in a patient, comprising administering to said patient a dose of 0.5 mg per day of LY3154207, or pharmaceutical composition thereof.

In an embodiment, the present invention provides LY3154207, or pharmaceutical composition thereof, for the manufacture of a medicament for use in the treatment of a dopaminergic central nervous system disorder in a patient, comprising administering to said patient a dose of 1 mg per day of LY3154207, or pharmaceutical composition thereof.

In an embodiment, the present invention provides LY3154207, or pharmaceutical composition thereof, for the manufacture of a medicament for use in the treatment of a dopaminergic central nervous system disorder in a patient, comprising administering to said patient a dose of 2 mg per day of LY3154207, or pharmaceutical composition thereof.

In an embodiment, the present invention provides LY3154207, or pharmaceutical composition thereof, for the manufacture of a medicament for use in the treatment of a dopaminergic central nervous system disorder in a patient, comprising administering to said patient a dose of 3 mg per day of LY3154207, or pharmaceutical composition thereof.

In an embodiment, the present invention provides LY3154207, or pharmaceutical composition thereof, for the manufacture of a medicament for use in the treatment of a dopaminergic central nervous system disorder in a patient, comprising administering to said patient a dose of 5 mg per day of LY3154207, or pharmaceutical composition thereof.

In an embodiment, the present invention provides LY3154207, or pharmaceutical composition thereof, for the manufacture of a medicament for use in the treatment of a dopaminergic central nervous system disorder in a patient, comprising administering to said patient a dose of 10 mg per day of LY3154207, or pharmaceutical composition thereof.

In an embodiment, the present invention provides LY3154207, or pharmaceutical composition thereof, for the manufacture of a medicament for use in the treatment of a dopaminergic central nervous system disorder in a patient, comprising administering to said patient a dose of 15 mg per day of LY3154207, or pharmaceutical composition thereof.

In an embodiment, the present invention provides LY3154207, or pharmaceutical composition thereof, for the manufacture of a medicament for use in the treatment of a dopaminergic central nervous system disorder in a patient, comprising administering to said patient a dose of 20 mg per day of LY3154207, or pharmaceutical composition thereof.

In an embodiment, the present invention provides LY3154207, or pharmaceutical composition thereof, for the manufacture of a medicament for use in the treatment of a dopaminergic central nervous system disorder in a patient, comprising administering to said patient a dose of 30 mg per day of LY3154207, or pharmaceutical composition thereof.

In an embodiment, the present invention provides LY3154207, or pharmaceutical composition thereof, for the manufacture of a medicament for use in the treatment of a dopaminergic central nervous system disorder in a patient, comprising administering to said patient a dose of 50 mg per day of LY3154207, or pharmaceutical composition thereof.

In an embodiment, the present invention provides LY3154207, or pharmaceutical composition thereof, for the manufacture of a medicament for use in the treatment of a dopaminergic central nervous system disorder in a patient, comprising administering to said patient a dose of 75 mg per day of LY3154207, or pharmaceutical composition thereof.

In an embodiment, the present invention provides LY3154207, or pharmaceutical composition thereof, for the manufacture of a medicament for use in the treatment of Parkinson's Disease in a patient, comprising administering to said patient a dose of about 0.5 mg to about 75 mg, up to a maximum total dose of 75 mg per day, of LY3154207, or pharmaceutical composition thereof.

In an embodiment, the present invention provides LY3154207, or pharmaceutical composition thereof, for the manufacture of a medicament for use in the treatment of Parkinson's Disease in a patient, comprising administering to said patient a dose of about 0.5 mg to about 15 mg, up to a maximum total dose of 15 mg per day, of LY3154207, or pharmaceutical composition thereof.

In an embodiment, the present invention provides LY3154207, or pharmaceutical composition thereof, for the manufacture of a medicament for use in the treatment of Parkinson's Disease in a patient, comprising administering to said patient a dose per day selected from the group consisting of 0.5 mg, 1 mg, 2 mg, 3 mg, 5 mg, 10 mg, 15 mg, 20 mg, 30 mg, 50 mg, and 75 mg, of LY3154207, or pharmaceutical composition thereof.

In an embodiment, the present invention provides LY3154207, or pharmaceutical composition thereof, for the manufacture of a medicament for use in the treatment of Parkinson's Disease in a patient, comprising administering to said patient a dose of about 0.5 mg to about 75 mg, up to a maximum total dose of 75 mg per day, of LY3154207, or pharmaceutical composition thereof, wherein the patient meets the revised MDS criteria for PD and mild-to-moderate dementia as defined by a decline in cognitive function with an MoCA score between 10 and 23.

In an embodiment, the present invention provides LY3154207, or pharmaceutical composition thereof, for the manufacture of a medicament for use in the treatment of Parkinson's Disease in a patient, comprising chronic daily administration to said patient a dose of about 0.5 mg to about 75 mg, up to a maximum total dose of 75 mg per day, of LY3154207, or pharmaceutical composition thereof, wherein the patient is treated for at least 21 consecutive days.

In an embodiment, the present invention provides LY3154207, or pharmaceutical composition thereof, for the manufacture of a medicament for use in the treatment of Alzheimer's Disease in a patient, comprising administering to said patient a dose of about 0.5 mg to about 75 mg, up to a maximum total dose of 75 mg per day, of LY3154207, or pharmaceutical composition thereof.

In an embodiment, the present invention provides LY3154207, or pharmaceutical composition thereof, for the manufacture of a medicament for use in the treatment of Alzheimer's Disease in a patient, comprising administering to said patient a dose of about 0.5 mg to about 15 mg, up to a maximum total dose of 15 mg per day, of LY3154207, or pharmaceutical composition thereof.

In an embodiment, the present invention provides LY3154207, or pharmaceutical composition thereof, for the manufacture of a medicament for use in the treatment of Alzheimer's Disease in a patient, comprising administering to said patient a dose per day selected from the group consisting of 0.5 mg, 1 mg, 2 mg, 3 mg, 5 mg, 10 mg, 15 mg, 20 mg, 30 mg, 50 mg, and 75 mg, of LY3154207, or pharmaceutical composition thereof.

In an embodiment, the present invention provides LY3154207, or pharmaceutical composition thereof, for the manufacture of a medicament for use in the treatment of Alzheimer's Disease in a patient, comprising chronic daily administration to said patient a dose of about 0.5 mg to about 75 mg, up to a maximum total dose of 75 mg per day, of LY3154207, or pharmaceutical composition thereof, wherein the patient is treated for at least 21 consecutive days.

In an embodiment, the present invention provides LY3154207, or pharmaceutical composition thereof, for the manufacture of a medicament for use in inducing weight loss in a patient, comprising administering to said patient a dose of about 0.5 mg to about 75 mg, up to a maximum total dose of 75 mg per day, of LY3154207, or pharmaceutical composition thereof.

In an embodiment, the present invention provides LY3154207, or pharmaceutical composition thereof, for the manufacture of a medicament for use in inducing weight loss in a patient, comprising administering to said patient a dose of about 0.5 mg to about 15 mg, up to a maximum total dose of 15 mg per day, of LY3154207, or pharmaceutical composition thereof.

In an embodiment, the present invention provides LY3154207, or pharmaceutical composition thereof, for the manufacture of a medicament for use in inducing weight loss in a patient, comprising administering to said patient a dose per day selected from the group consisting of 0.5 mg, 1 mg, 2 mg, 3 mg, 5 mg, 10 mg, 15 mg, 20 mg, 30 mg, 50 mg, and 75 mg, of LY3154207, or pharmaceutical composition thereof.

In an embodiment, the present invention provides LY3154207, or pharmaceutical composition thereof, for the manufacture of a medicament for use in inducing weight loss in a patient, comprising chronic daily administration to said patient a dose of about 0.5 mg to about 75 mg, up to a maximum total dose of 75 mg per day, of LY3154207, or pharmaceutical composition thereof, wherein the patient is treated for at least 21 consecutive days.

As used above, and throughout the description of the invention, the following terms, unless otherwise indicated, shall be understood to have the following meanings:

A "pharmaceutically acceptable carrier, diluent, or excipient" is a medium generally accepted in the art for the delivery of biologically active agents to mammals, e.g., humans.

A "dose" refers to a predetermined quantity or unit dose of LY3154207 calculated to produce the desired therapeutic effect in a patient. As used herein "mg" refers to milligram. As used herein, dose ranges and doses provided of LY3154207 represent the weight of the active pharmaceutical ingredient, 2-(2,6-dichlorophenyl)-1-[(1S,3R)-3-(hydroxymethyl)-5-(3-hydroxy-3-methylbutyl)-1-methyl-3,4-dihydroisoquinolin-2 (1H)-yllethanone, regardless of the form in which it is provided, such as the free base, a cocrystalline form, or any other composition or form. Preferably unit doses are comprised of 2-(2,6-dichlorophenyl)-1-[(1S,3R)-3-(hydroxymethyl)-5-(3-hydroxy-3-methylbutyl)-1-methyl-3,4-dihydroisoquinolin-2 (1H)-ylJethanone and 4-hydroxy benzoic acid in cocrystalline form. The term "about" as used herein, means in reasonable vicinity of the stated numerical value, such as plus or minus 10% of the stated numerical value.

Methods of making and formulating LY3154207 and/or 2-(2,6-dichlorophenyl)-1-((1S,3R)-5-(2-hydroxy-2-methylpropyl)-3-(hydroxymethyl)-1-methyl-3,4-dihydroisoquinolin-2 (1H)-yl) ethan-1-one, are known in the art and recited for example in WO 2014/193781 and/or WO 2017/070068. Methods of preparing LY3154207 and co-crystals thereof, and certain formulations and dosage forms thereof, are known to the skilled artisan, and are described in WO 2014193781 and/or WO 2017/070068. WO 2014/193781 discloses certain 3,4-dihydroisoquinolin-2 (1H)-yl compounds as positive allosteric modulators (PAM) of the dopamine 1 receptor (DI), including 2-(2,6-dichlorophenyl)-1-[(1S,3R)-3-(hydroxymethyl)-5-(3-hydroxy-3-methylbutyl)-1-methyl-3,4-dihydroisoquinolin-2 (1H)-ylJethanone and a cocrystalline form comprising 2-(2,6-dichlorophenyl)-1-[(1S,3R)-3-(hydroxymethyl)-5-(3-hydroxy-3-methylbutyl)-1-methyl-3,4-dihydroisoquinolin-2 (1H)-ylJethanone and 4-hydroxy benzoic acid, and compositions thereof. WO 2017/070068 discloses crystalline 2-(2,6-dichlorophenyl)-1-[(1S,3R)-3-(hydroxymethyl)-5-(3-hydroxy-3-methylbutyl)-1-methyl-3,4-dihydroisoquinolin-2 (1H)-yllethanone. LY3154207 is preferably formulated as pharmaceutical composition administered by any route which makes the compound bioavailable, including oral, intravenous, and transdermal routes. Most preferably, such pharmaceutical compositions are for oral administration. LY3154207 can be administered alone or in the form of a pharmaceutical composition with pharmaceutically acceptable carriers, diluents or excipients. Throughout the description, where compositions are described as having, including, or comprising specific components, it is contemplated that compositions also consist essentially of, or consist of, the recited components. Such pharmaceutical compositions and processes for making the same are known in the art (See, e.g., Remington: The Science and Practice of Pharmacy, L. V. Allen, Editor, 22nd Edition, Pharmaceutical Press, 2012). In a formulation LY3154207 is usually mixed with an excipient, diluted by an excipient, or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the formulations can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, gels, suppositories, sterile injectable solutions, and sterile packaged powders. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents: emulsifying and suspending agents: preserving agents such as methyl- and propylhydroxy benzoates: sweetening agents; and flavoring agents. The compounds of the invention can be formulated so as to provide quick, sustained or delayed release of the active ingredient after administration to the patient by employing procedures known in the art. One skilled in the art of preparing formulations can readily select the proper form and mode of administration depending upon the particular characteristics of the compound and/or form selected, the disorder or condition to be treated, the stage of the disorder or condition, and other relevant circumstances. The table below provides examples of selected unit dosage forms provided as tablets for oral administration according to the dosing regimens of the present invention. The skilled artisan can use these examples, along with readily known formulation methods, to provide additional formulations and/or unit dosage forms.

| | Unit Dose (mg LY3154207, active ingredient) | | | | | | | |
|---|---|---|---|---|---|---|---|---|
| Component | 1 mg | 3 mg | 5 mg | 10 mg | 25 mg | 30 mg | 50 mg | 75 mg |
| LY3154207-Benzoic Acid Cocrystal (mg) | 1.3 | 3.9 | 6.5 | 13.1 | 32.7 | 39.2 | 65.3 | 98 |
| Microcrystalline Cellulose | 116.8 | 112.3 | 109.7 | 126.4 | 81.1 | 142.8 | 162.2 | 243.3 |

-continued

| | Unit Dose (mg LY3154207, active ingredient) | | | | | | | |
|---|---|---|---|---|---|---|---|---|
| Component | 1 mg | 3 mg | 5 mg | 10 mg | 25 mg | 30 mg | 50 mg | 75 mg |
| Croscarmellose Sodium | 6.3 | 6.3 | 6.3 | 7.5 | 6.3 | 10 | 12.5 | 18.8 |
| Sodium Stearyl Fumarate | 0.6 | 2.5 | 2.5 | 3 | 2.5 | 4 | 5 | 7.5 |
| Silixon Dioxide, | 0 | 0 | 0 | 0 | 2.5 | 4 | 5 | 7.5 |
| Core Tablet Weight (mg): | 125 | 125 | 125 | 150 | 125 | 200 | 250 | 375 |
| Coating: | 4 | 5 | 5 | 6 | 5 | 8 | 10 | 15 |

The unit doses of the present invention are formulated as pharmaceutical compositions administered by any route which makes the compound bioavailable, preferably such compositions are for oral administration. "Administration" or "administering", as used herein, includes wherein the patient self-administers LY3154207, and/or wherein LY3154207 is administered by another person, and/or wherein the patient is instructed and/or directed to consume LY3154207 according to a particular regimen. Preferably LY3154207 is administered in the morning. Preferably the indicated unit doses of LY3154207 are taken one time per day, as is indicated by the use of the term "per day". Preferably, LY3154207 is taken daily. As used herein, "daily administration" includes the administration of LY3154207 as a specific treatment regimen intended to provide the beneficial effect from the long term and regular administration of LY3154207 at the specified doses. In particular, "daily administration" includes administration every day consecutively for not less than twenty one days in a row, or for as long as is needed to prevent the patients' signs and symptoms of a dopaminergic CNS disorder. If a patient misses an occasional day, then the patient may simply resume administration on the next day specified for administration, and such an instance would continue to represent "daily administration". As used herein, "daily" means LY3154207 is administered one time every 24-hour period, or one time every calendar day. As used herein, "daily" means LY3154207 is administered on an ongoing consecutive basis, where administering includes as used herein includes both when the patient administers the doses, and/or wherein the patient is instructed to administer the doses as part of a treatment regimen. Where methods are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

As used herein, the term "patient" refers to a human, and patients to be treated by the present dosing regimens are dopaminergic CNS disorder patients, and as such share etiophathological aspects, wherein disturbances of dopamine signaling are known to contribute to these diseases. As used herein dopaminergic CNS disorders include, but are not limited to, Parkinson's Disease, Alzheimers' Disease, Lewy body dementia (LBD), Vascular Dementia, Schizophrenia, ADHD, Depression, Autism, chronic musculoskeletal pain, fibromyalgia, cognitive impairment disorders, sleep disorders, excessive daytime sleepiness, narcolepsy, shift work disorder, traumatic brain injury, chronic traumatic encephalopathy, obesity and appetite regulation, mood disorders, lethargy, apathy, and addiction disorders. Identification of patients with these dopaminergic CNS disorders can be achieved by established methods known to the skilled artisan.

In embodiments of the invention a patient is a human who has been diagnosed as having a medical risk, condition or disorder, such as a dopaminergic CNS disorder, in need of treatment with a dosing regimen described herein. In those instances where the disorders which can be treated by the methods of the present invention are known by established and accepted classifications, such as AD, PD, LBD, their classifications can be found in various well-known medical texts. For example, at present, the 5th edition of the Diagnostic and Statistical Manual of Mental Disorders (DSM-5), provides a diagnostic tool for identifying many of the disorders described herein. Also, the International Classification of Diseases, Tenth Revision (ICD-10), provides classifications for many of the disorders described herein. The skilled artisan will recognize that there are alternative nomenclatures, nosologies, and classification systems for disorders described herein, including those as described in the DSM-5 and ICD-10, and that terminology and classification systems evolve with medical scientific progress. Cognitive impairment in subjects with Parkinson's disease is commonly referred to as neurocognitive disorder. Diagnostic criteria in DSM-5 (5th edition of the Diagnostic and Statistical Manual of Mental Disorders) describe evidence of significant cognitive decline from a previous level of performance (concern of individual or informant documented by neuropsychological testing), and the cognitive deficits may or may not interfere with independence in everyday activities. This is qualified as major or mild neurocognitive disorder. "Weight loss" as used herein refers to a reduction in body weight, and/or to chronic weight management wherein treatment promotes maintenance of body weight within a desired range.

The terms "treatment" and "treating" are intended to refer to all processes wherein there may be a slowing, interrupting, arresting, controlling, or stopping of the progression of an existing disorder and/or symptoms thereof, but does not necessarily indicate a total elimination of all symptoms.

The attending diagnostician, as one skilled in the art, can readily determine the dose chosen from the dosing regimens provided herein by observing results obtained from treatment. In determining a specific dose of LY3154207 from dosing regimens of the present invention, a number of factors are considered, including, but not limited to the dopaminergic CNS disorder from which the patient suffers, the weight, age, and general health of the patient: the degree of involvement or the severity of the disorder: the response of the 20 individual patient: the use of other concomitant medication; and other relevant circumstances.

A dose regimen of the present invention may be used in combination with other drugs that are used in the treatment/prevention/suppression or amelioration of a dopaminergic CNS disorder. Such other drug(s) may be administered, by a route and in an amount commonly used therefore, contemporaneously or sequentially with LY3154207. For example, other active ingredients effective in the treatment of Parkinson's disease that may be combined with LY3154207, include, but are not limited to: (a) dopamine precursors such as levodopa: melevodopa, and etilevodopa; and (b) dopamine agonists including pramipexole, ropinirole, apomorphine, rotigotine, bromocriptine, cabergoline, and pergolide.

BRIEF DESCRIPTION OF THE DRAWINGS

FIG. 3: Design of the study HBEC, a multiple ascending dose study of LY3154207, a randomized, double-blind, placebo-controlled, multiple ascending dose, parallel-group study, of healthy subjects (Part A) and participants with PD (Part B) who received once-daily doses of LY3154207 (15, 30, 75, or 150 mg in Part A and up to 75 mg in Part B) or placebo for 14 days. aEach ascending dose cohort commenced only after review of the safety data to at least Day 7 from the previous cohort. bParticipants with PD in Cohort 6 received titrated doses to determine the effect of this dosing schedule (i.e., Days 1-3:15 mg: Days 4-6:30 mg; and Days 7-14:75 mg) on cardiovascular effects. Note: All cohorts were dosed for 14 days. CRU=clinical research unit: LY=LY3154207; PBO=placebo: PD=Parkinson's disease: R=randomized.

Example 1: Phase I Clinical Studies of LY3154207

LY3154207 is currently in phase 2 for cognition in Lewy Body Dementias (NCT03305809). Prior data from 3 completed clinical pharmacology phase I studies of LY3154207, Studies HBEA, HBEB, and HBEC, provide evidence of the concept for use of LY3154207 in the treatment of a dopaminergic central nervous system disorder in a patient, comprising administering to said patient a dose of about 0.5 mg to about 75 mg, up to a maximum total dose of 75 mg per day, of LY3154207, or pharmaceutical composition thereof.

Figure 1:
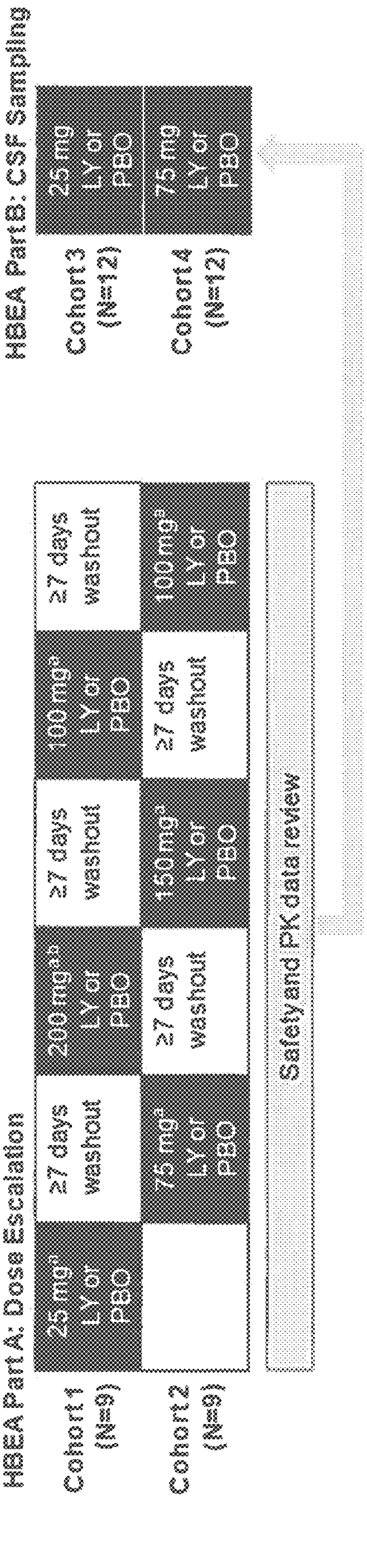
FIG. 1: Design of the study HBEA, a single ascending dose study of a D1 receptor positive allosteric modulator LY3154207 in healthy volunteers. aSafety review completed after each dose level prior to escalation. bDose escalation was terminated at 200 mg owing to cardiovascular effects. CSF=cerebrospinal fluid: LY=LY3154207: PBO=placebo: PK-pharmacokinetic.

HBEA is a single ascending dose study of a D1 receptor positive allosteric modulator LY3154207 in healthy volunteers. Study HBEA aims to determine the safety, tolerability, and peripheral and central pharmacokinetics (PK) of single ascending doses of LY3154207 in healthy subjects. Study HBEB aims to evaluate the effect of single-dose LY3154207 on sleep latency in sleep-deprived healthy male subjects as measured by a multiple sleep latency test (MSLT). HBEA was a Phase 1, 2-part, randomized, double-blind, placebo-controlled study in healthy males or females. Part A has a 3-period crossover design with 2 alternating, single-dose escalating cohorts, and subjects were randomized to LY3154207 (n=6) or placebo (n=3) in each cohort in each dosing period. Part B has a single-period, single-dose, 2-cohort design with cerebrospinal fluid (CSF) sampling, and subjects were randomized to LY3154207 (n=8) or placebo (n=4) in each cohort. Design of the study is shown in FIG. 1.

HBEA Part A-Single Ascending Dose (SAD) Study

This is a phase 1, SAD, crossover design of LY3154207 in healthy subjects conducted in 2 alternating cohorts with dose escalation. Subjects are dosed at 25 mg, 75 mg, 100 mg, 150 mg and 200 mg or placebo. Safety parameters assessed include adverse events (AEs), safety laboratories, vital signs, ambulatory blood pressure monitoring (ABPM) and electrocardiogram (ECG). Subjects provide blood samples after dosing to measure plasma concentrations of LY3154207 for assessment of PK.

Eighteen subjects enrolled with 17 subjects completing the study. Subjects had a mean age (SD) of 33.6 (13.0), 16 were male (89%) and 16 white (89%). One subject withdrew due to anxiety following a 150 mg dose. A total of 111 treatment emergent AEs occurred and were mostly mild (101/111). Insomnia, decreased appetite, anxiety, dizziness, headache, nausea, upper abdominal pain, and dysgeusia were the most common AEs and the majority (69/111) occurred at doses ≥100 mg. A dose-related signal for increases in pulse and blood pressure occurred and resolved in 24 hours. The Cmax and AUC was proportional with dose administered. The median tmax and the t 1/2 were approximately 2-3 and 12 hours, respectively. The administered LY3154207 dose excreted in urine was 0.02%. Over the dose range of 25-200 mg, LY3154207 demonstrates an acceptable safety profile and a linear PK profile. This data from Phase 1 in healthy volunteers suggests that the dosing regimens of the present invention may provide appetite reducing effects in dopaminergic central nervous system disorders or healthy subjects. Data indicating a dose-related signal for increases in pulse and blood pressure also indicate the dosing regimens of the present invention may provide an improved combination of efficacy, safety, and clinical tolerability for use of LY3154207 which can avoid and/or minimize these undesirable effects. LY3154207 was well tolerated with an increase in AEs associated with central activation at doses ≥75 mg. In HBEA Part A, treatment-related adverse events (AEs) occurred primarily at doses ≥100 mg and were mostly mild. In HBEA Part B, treatment-related AEs occurred only at 75 mg (25% of subjects) and were all mild: energy increased, anxiety, decreased appetite, and dizziness. No serious or severe AEs occurred. LY3154207 produced a dose-related increase in ambulatory blood pressure monitoring (ABPM) blood pressure and pulse rate, with preservation of the diurnal rhythm. Dose-related increases in systolic and diastolic blood pressure and pulse rate were seen from ABPM, peaking between 4 and 12 hours post-dose and mostly resolving within 24 hours. Based on ABPM, the 4- to 8-hour estimates of the difference in least squares means for LY3154207 200 mg vs. placebo were 32 beats per minute (bpm) for pulse rate, and 14 mm Hg and 10 mm Hg for systolic and diastolic blood pressure, respectively. Results are shown in Table A.

TABLE A

| HBEA Part A | Placebo (N = 18) | LY 25 mg (N = 6) | LY 75 mg (N = 6) | LY 100 mg (N = 8) | LY 150 mg (N = 9) | LY 200 mg (N = 6) |
|---|---|---|---|---|---|---|
| Treatment-related AEs, n (%) [events] | 5 (27.8) [6] | 1 (16.7) [1] | 4 (66.7) [8] | 6 (75.0) [17] | 8 (88.9) [34] | 5 (83.3) [18] |
| Insomnia[a] | 0 | 0 | 1 [1] | 4 [4] | 3 [3] | 3 [3] |
| Decreased appetite[a] | 1 [1] | 0 | 1 [1] | 1 [1] | 3 [3] | 2 [2] |
| Anxiety[a] | 0 | 0 | 0 | 2 [2] | 3[b] [4] | 1 [1] |
| Dizziness[a] | 0 | 0 | 2 [2] | 1 [1] | 2 [2] | 1 [1] |
| Nausea[a] | 1 [1] | 0 | 0 | 0 | 2 [2] | 2 [2] |
| Dysgeusia[a] | 0 | 0 | 0 | 2 [2] | 2 [2] | 0 |
| Energy increased[a] | 0 | 0 | 0 | 1 [1] | 1 [1] | 1 [1] |
| Feeling hot[a] | 0 | 0 | 0 | 1 [1] | 1 [1] | 1 [1] |
| Headache[a] | 0 | 0 | 1 [1] | 0 | 2 [2] | 0 |

[a]Treatment-related AEs in ≥3 subjects.
[b]One subject discontinued owing to an AE of anxiety following LY3154207 150 mg.
AE = adverse event;
LY = LY3154207.

Doses of LY3154207≤75 mg had acceptable safety and tolerability. LY3154207 produced a dose-related increase in blood pressure and pulse rate measured by ABPM, with preservation of the diurnal rhythm.

HBEA Part B-Cerebrospinal Fluid

HBEA Part B is a study of Cerebrospinal fluid (CSF) and plasma pharmacokinetic (PK) profile following a single dose of LY3154207 in healthy volunteers. The objective of the study is to determine the CSF and plasma PK profile of LY3154207 in a single dose study m healthy volunteers. This study consisted of 2 cohorts in a single-dose, single-period, placebo-controlled, randomized, double-blind, parallel-group study. Subjects were randomized to 25 mg and 75 mg and underwent serial blood and CSF sampling at 2 hours pre-dose and 24 hours post-dose to measure concentrations of LY3154207. Twenty-four subjects enrolled and all completed the study. Subjects had a mean age (SD) of 29.4 (9.8) and 22 were male (92%) and 22 were white (92%). Concentrations of LY3154207 in CSF were detectable up to 8 h after a dose of 25 mg and up to 24 hours after a dose of 75 mg. At each dose about 1% of the total LY3154207 exposure in plasma was available in CSF. At 25 mg and 75 mg, central penetration of LY3154207 was confirmed by measurement of LY3154207 in CSF supporting its use according to the dosing regimens of the present invention in dopaminergic CNS disorders. LY3154207 demonstrated linear plasma PK and evidence of central penetration.

LY3154207 showed linear plasma PK with median time of maximum concentration (tmax) approximately 2-3 hours, terminal half-life (t1/2) approximately 12 hours, apparent clearance (CL/F) 19-25 L/h across doses, and negligible renal elimination. Maximum concentration (Cmax) and area under the concentration versus time curve from time 0 to infinity ($AUC_{0-\infty}$) increased in proportion to LY3154207 dose, from 25 to 200 mg. In CSF, LY3154207 median tmax was 3-4 hours and t1/2 was 8 hours. About 1% of the total LY3154207 exposure in plasma was available in CSF, with a CSF/unbound plasma ratio of 0.3. Central penetration of LY3154207 was thus confirmed by CSF PK at 25 and 75 mg doses of HBEA Part B.

HBEB Phase I Sleep Latency Study in Healthy Volunteers

Figure 2:
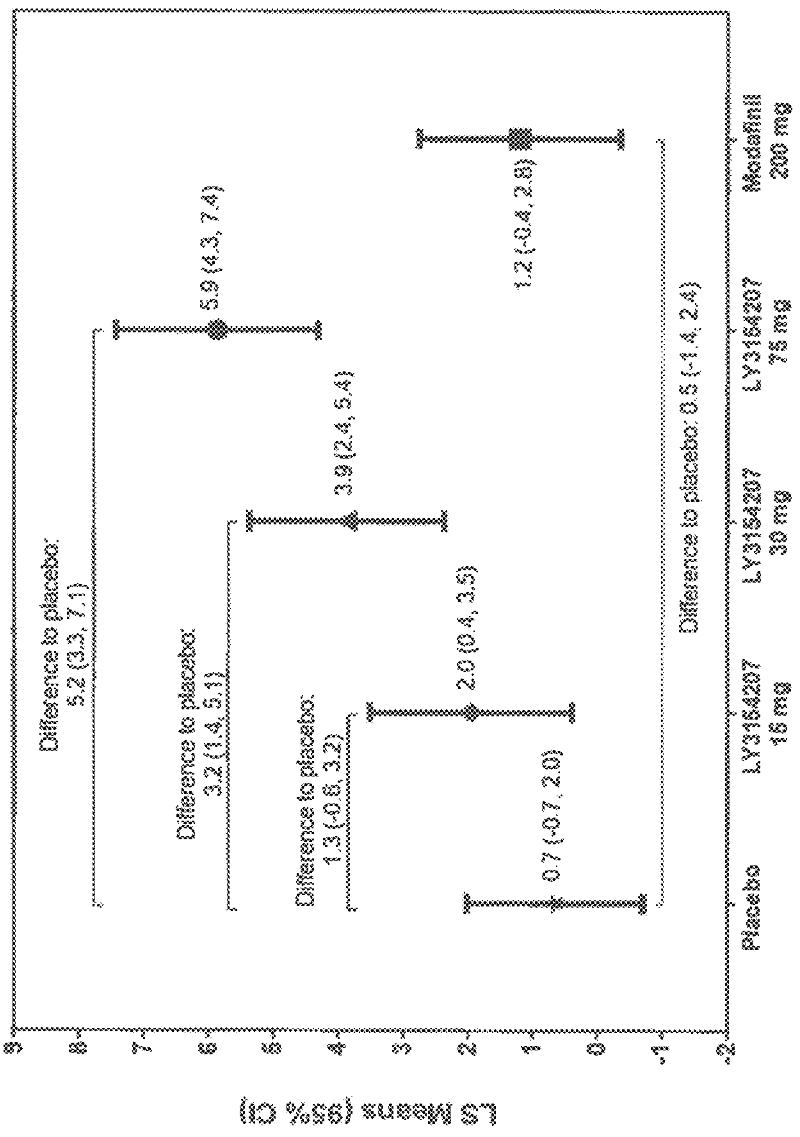
FIG. 2: HBEB, a Phase 1, single-dose, randomized, placebo-controlled, 4-period, incomplete crossover study in sleep-deprived healthy male subjects (n=17). Effects of a single dose of LY3154207 on wakefulness as measured by the multiple sleep latency test (MSLT) in sleep deprived healthy male subjects. Sleep latency is time from start of MSLT to first detection of sleep (minutes). If a subject did not sleep during the MSLT period, a sleep latency of 20 minutes was recorded. CI=confidence interval: LS-least squares: MSLT=multiple sleep latency test.

Dose dependent activating adverse events were also observed in a single ascending dose study. To determine the effects of a single dose of LY3154207 was studied on wakefulness as measured by the multiple sleep latency test (MSLT) in sleep deprived healthy male subjects. HBEB was a Phase 1, single-dose, randomized, placebo-controlled, 4-period, incomplete crossover study in sleep-deprived healthy male subjects (n=17). Subjects were randomized to receive a single dose of either placebo, LY3154207 15, 30, or 75 mg (double-blind), or modafinil (open-label control). In each period, subjects were sleep deprived for approximately 26 hours before dosing and approximately 12 hours post-dose. MSLT was conducted every 2 hours until 10 hours post-dose. Analysis based on mixed-model repeated measures included treatment, period, time, and the treatment-by-time interaction as fixed effects, and subject as a random effect: overall sleep latency was the average of the 4 post-dose sleep latencies. All subjects are randomized to receive 4 out of 5 available single dose treatments (15, 30, 75 mg LY3154207, placebo or modafanil 200 mg) with all subjects receiving placebo. The washout period is at least 7 days. MSLT is the primary assessment of wakefulness. Secondary outcomes include the Karolinska Sleepiness Scale (KSS), EEG and a simple reaction performance task. Blood samples are collected to measure plasma concentrations of LY3154207 and modafinil. Seventeen subjects are enrolled and received at least one dose of study drug with sixteen subjects completing all 4 periods of the trial. A dose dependent increase in MSLT is observed with least square means (95% CI) difference compared to placebo of 5.2 minutes (3.3,7.1) for 75 mg, 3.2 minutes (1.4, 5.1) for 30 mg, 1.3 minutes (−0.6, 3.2) for 15 mg, as shown in FIG. 2. LY3154207 also demonstrated a dose-dependent increase in alertness measured by the Karolinska sleepiness scale. PK is linear with a Cmax and t1/2 of approximately 3 and 9 hours across the dose range. These results are depicted in FIG. 2. LY3144207 increases wakefulness in sleep-deprived healthy volunteers which provides human clinical evidence of D1 receptor signaling engagement, and resulting wake promotion, in a phase 1 sleep latency study (HBEB). Central pharmacodynamic activity was thus confirmed through a dose-dependent increase in wakefulness. The HBEB Phase I sleep latency study in healthy volunteers demonstrates that LY3154207 improves wakefulness in a dose dependent manner in sleep deprived healthy males, supporting the use of LY3154207 in disorders associated with excessive daytime sleepiness and other dopaminergic central nervous system disorders, according to the dosing regimens of the present invention.

HBEC, A Multiple Ascending Dose Study of LY3154207:

In this randomized, double-blind, placebo-controlled, multiple ascending dose, parallel-group study, HBEC, healthy subjects (Part A) and participants with PD (Part B) received once-daily doses of LY3154207 (15, 30, 75, or 150 mg in Part A and up to 75 mg in Part B) or placebo for 14 days, as illustrated in FIG. 3.

Study outcomes included 24-hour ambulatory blood pressure monitoring (ABPM), treatment-emergent adverse events (TEAEs), and PK assessments in both healthy subjects and participants with PD, as well as Movement Disorder Society-United Parkinson's Disease Rating Scale (MDS-UPDRS) assessments to evaluate the impact of LY3154207 on motor function in participants with PD. The objective was to explore the safety, tolerability, and pharmacokinetics (PK) of multiple oral daily dosing of LY3154207 in healthy subjects (Part A) and in participants with PD (Part B).

Study HBEC Part a: Cognition Results from Phase 1 in Healthy Volunteers and Motor Symptoms in PD Patients in 14-Day Treatment with LY3154207

In healthy subjects and participants with PD, TEAEs were mostly mild with no severe or serious TEAEs or TEAEs leading to discontinuation. In participants with PD receiving LY3154207, treatment-related adverse events (AEs) were upper abdominal pain (n=1), visual hallucination (n=1), headache (n=1), and hypoesthesia (n=1). In healthy subjects, the incidence of TEAEs showed a dose-dependent increase following multiple dosing with LY3154207. In healthy subjects receiving LY3154207, common treatment-related AEs (primarily at the 150 mg dose) were insomnia (n=4), dizziness (n=3), nervousness (n=3), palpitations (n=3), and nausea (n=2). In participants with PD, the effects of LY3154207 on vital signs were less clear than in healthy subjects. Results are shown in Table B. Multiple once-daily doses of LY3154207 up to 150 mg in healthy subjects and up to 75 mg in participants with PD were well tolerated. The initial increase in SBP, DBP, and pulse rate observed with initial administration of LY3154207 showed accommodation with repeated dosing in both healthy subjects and participants with PD, although accommodation effect was less notable in participants with PD. The PK properties of LY3154207 were generally similar between healthy subjects and participants with PD, although a slight increase in LY3154207 exposure was observed in participants with PD.

TABLE B

| | Healthy Subjects | | | | | | Participants With PD | | | |
|---|---|---|---|---|---|---|---|---|---|---|
| | PBO (N = 12) | LY 15 mg (N = 9) | LY 30 mg (N = 9) | LY 75 mg (N = 9) | LY 150 mg (N = 9) | Total (N = 48) | PBO (N = 8) | LY 75 mg (N = 9) | LY 75 mg Titration[a] (N = 8) | Total (N = 25) |
| Subjects with ≥1 TEAE, n (%) | 5 (41.7) | 4 (44.4) | 5 (55.6) | 3 (33.3) | 8 (88.9) | 25 (52.1) | 3 (37.5) | 6 (66.7) | 5 (62.5) | 14 (56.0) |
| Number of TEAEs | 5 | 6 | 5 | 6 | 35 | 57 | 5 | 14 | 7 | 26 |
| Mild | 5 | 6 | 5 | 6 | 35 | 57 | 4 | 13 | 6 | 23 |
| Moderate | 0 | 0 | 0 | 0 | 0 | 0 | 1 | 1 | 1 | 3 |

[a]Participants with PD received titrated doses: Days 1-3: 15 mg; Days 4-6: 30 mg; and Days 7-14: 75 mg.
LY = LY3154207;
PBO = placebo;
PD = Parkinson's disease;
TEAE = treatment-emergent adverse event.

Figure 4:
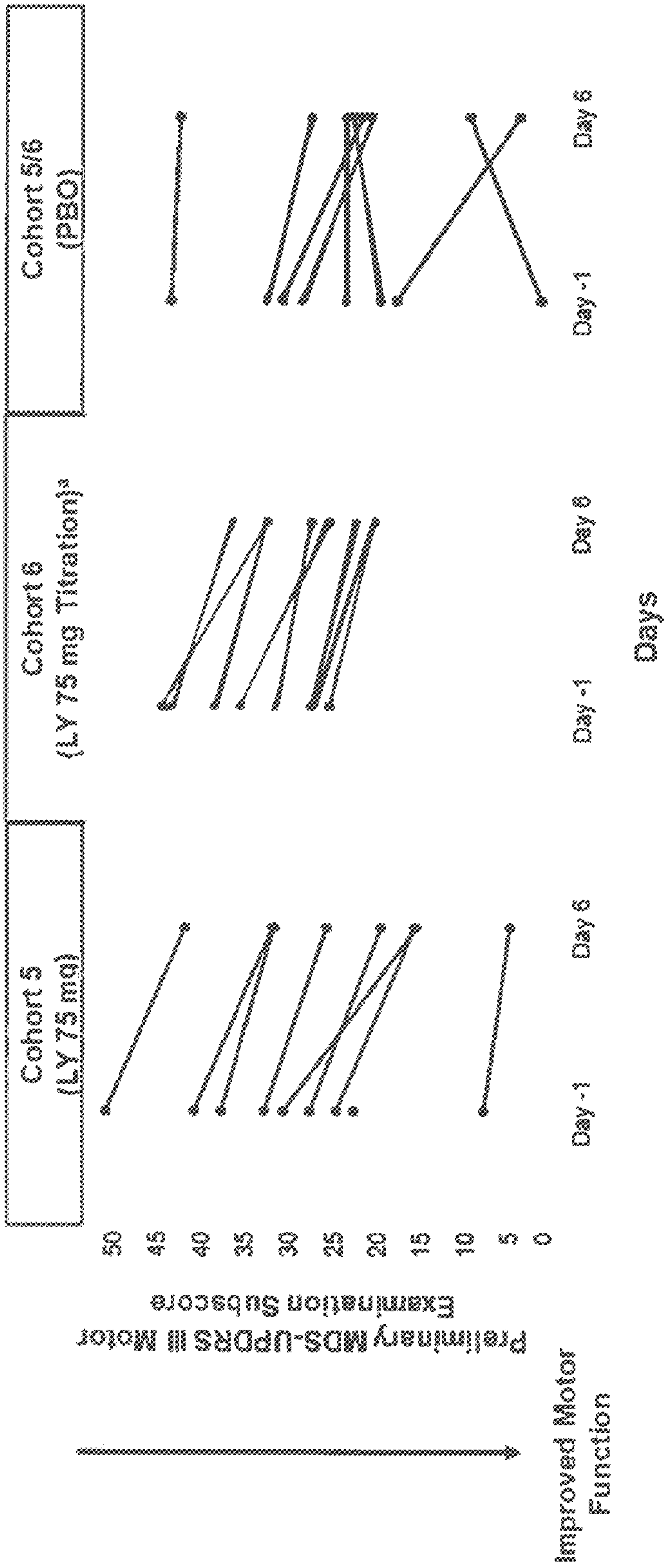
FIG. 4: Study HBEC, motor symptoms in PD patients in 14-day treatment with LY3154207. Participants with PD, treated with LY3154207, motor examination subscores compared to those treated with placebo, as measured by MDS-UPDRS Part III. Cohort 5 (LY 75 mg), Cohort 6 (LY 75 mg titration) (Participants with PD in Cohort 6 received 15 mg on Days 1-3 and 30 mg on Days 4-6), Cohort 5/6 (PBO).

As shown in FIG. 4, Participants with PD treated with LY3154207 demonstrated a more consistent improvement in the motor examination subscore than those treated with placebo, as measured by MDS-UPDRS Part III, suggesting potential efficacy for motor symptoms in PD.

PK parameters of LY3154207 in healthy subjects and participants with PD demonstrate dose-dependent increases in exposure and minimal accumulation upon repeated dosing. Exposure of LY3154207 in Healthy Subjects and Participants With PD on Day 14 after LY3154207 75 mg show increases in Cmax and AUC (0-24) of 25% and 42%, respectively, in participants with PD.

TABLE C

| | Healthy Subjects (Day 14) | | | | Participants With PD (Day 14) | |
|---|---|---|---|---|---|---|
| | LY 15 mg (N = 9) | LY 30 mg (N = 9) | LY 75 mg (N = 9) | LY 150 mg (N = 9) | LY 75 mg (N = 8) | LY 75 mg Titration[a] (N = 8) |
| $C_{max}$, ng/ml | 66.2 | 149 | 307 | 500 | 335 | 400 |
| $t_{max}$, hours, median | 2.0 | 2.0 | 2.0 | 3.0 | 2.0 | 2.5 |
| $AUC_{(0-24)}$, ng · h/mL | 492 | 1240 | 2220 | 4350 | 3050 | 3680 |
| $CL_{ss}/F$, L/h | 30.5 | 24.2 | 33.8 | 34.5 | 24.6 | 20.4 |

TABLE C-continued

| | Healthy Subjects (Day 14) | | | | Participants With PD (Day 14) | |
|---|---|---|---|---|---|---|
| | LY 15 mg (N = 9) | LY 30 mg (N = 9) | LY 75 mg (N = 9) | LY 150 mg (N = 9) | LY 75 mg (N = 8) | LY 75 mg Titration[a] (N = 8) |
| $R_AC_{max}$[b] | 1.18 | 1.12 | 1.13 | 0.92 | 1.05 | NC |
| $R_AAUC_{(0-24)}$[b] | 1.34 | 1.03 | 0.99 | 0.93 | 1.06 | NC |
| $CL_r$, L/h | NC | 0.0036 | 0.0024 | 0.0034 | NC | NC |

[a]Participants with PD received titrated doses: Days 1-3: 15 mg; Days 4-6: 30 mg; and Days 7-14: 75 mg.
[b]The accumulation ratio was Day 14:Day 1.
Note:
All reported values in the table are geometric means unless otherwise specified.
AUC(0-24) = area under the concentration versus time curve from 0 to 24 hours;
CLr = renal clearance;
CLss/F = apparent total body clearance of drug at steady state calculated after extravascular administration;
Cmax = maximum drug concentration;
LY= LY3154207;
NC = not calculated;
PD = Parkinson's disease;
RA = accumulation ratio (Day 14:Day 1);
tmax = time to maximum drug concentration.

In the Digit Symbol Substitution Test (DSST)-All arms (including placebo) improve over time with greatest improvement from baseline seen at Day 13 assessment suggesting a learning effect is still present at Day 13. The LY3154207 15 mg dose, the lowest dose of LY tested, surprisingly gave the highest average change from baseline at both post dose time points. The Hopkins Verbal Learning Test (HVLT) provided some evidence of an inverse dose response relationship, where LY3154207 15 mg resulted in the largest average improvement from baseline. This data from Phase 1 in healthy volunteers suggests that the low dose range dosing regimen, up to 15 mg maximum total dose per day, may provide pro-cognitive effects in dopaminergic central nervous system disorders or healthy subjects.

Abbreviations: AUC(0)-24)-area under the concentration versus time curve from 0 to 24 hours. $AUC_{0-\infty}$=area under the concentration versus time curve from time 0 to infinity: CI=confidence interval: CL/F=apparent clearance: CLr-renal clearance: CLss/F=apparent total body clearance of drug at steady state calculated after extravascular administration: Cmax=maximum concentration: tmax-time to maximum drug concentration: CSF=cerebrospinal fluid: LS=least squares: LY=LY3154207: MSLT=multiple sleep latency test: PBO=placebo: PK-pharmacokinetics: t1/2=terminal half-life: tmax=time of maximum concentration. bpm-beats per minute: DBP=diastolic blood pressure: SBP-systolic blood pressure: LS=least squares: LY=LY3154207: MDS-UPDRS=Movement Disorder Society-United Parkinson's Disease Rating Scale: NC-not calculated: PD=Parkinson's disease: RA=accumulation ratio (Day 14: Day 1): AE-adverse event: TEAE=treatment-emergent adverse event.

Example 2: Spatial Working Memory in the Adult Rhesus Monkey

It has been established that the core cognitive function of working memory has a strong dependence on D1 receptor signaling in prefrontal cortex. While D1 agonists have presented pharmaceutical problems due to excessive stimulation and tolerance, D1 positive allosteric modulators (PAMs) may show promise in selectively enhancing pertinent DI activity in response to the spatiotemporal dynamics of dopamine transmission and hence may avoid these issues. The D1 PAM compound referred to as DPTQ or LY3151944, which is 2-(2,6-dichlorophenyl)-1-((1S,3R)-5-(2-hydroxy-2-methylpropyl)-3-(hydroxy methyl)-1-methyl-3,4-dihydroisoquinolin-2 (1H)-yl) ethan-1-one, is shown below, and surprisingly shows sustained improvement in spatial working memory in the adult rhesus monkey.

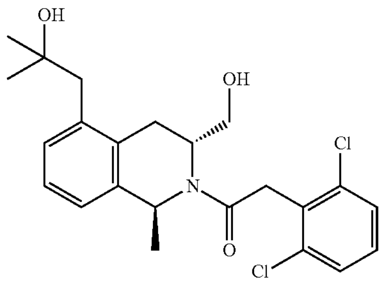 [SMILES: C[C@H]1c2cccc(CC(C)(C)O)c2C[C@H](CO)N1C(=O)Cc1c(Cl)cccc1Cl]

DPTQ showed a trend in reducing spatial working memory performance in the rhesus macaque monkey at acute doses of 2.5 to 10 mg/kg IM, but had little effect in protecting against ketamine induced cognitive deficits. However, despite this apparent lack of acute pro-cognitive effects, a surprisingly consistent and significant effect on performance was noticed when tested in the days following administration. Specifically, performance was substantially impaired 24 to 48 hours post injection but considerably enhanced when tested at 96 to 120 hours later.

Studies were done to assess the effects of low doses of DPTQ alone at 0.1, 1.0, and 10.0 mg/kg, as well as the effects of a single dose of 2.5 mg/kg repeated at the time of the delayed cognitive enhancement. It was observed that there is a modest degree of dose dependency in the magnitude of the delayed diminution and enhancement of cognition which may provide critical insights for therapeutic efficacy. It was discovered that when the dose of 2.5 mg/kg was repeated at the time of enhancement, a transient deficit could be invoked that later gave way to a prolonged enhancement in cognition. This unique and unexpected finding demonstrates the impact of chronicity and intermittency in repeated administration.

Experimental Overview: A group of both aged and non-aged animals was tested at a single dose of 2.5 mg/kg and their performance was followed daily for the first six days and on alternate days thereafter. This was to ascertain that we could repeat the effects we observed previously at the lowest possible dose. The effects of repeating this dose on Day 5, at the 120 hr mark, were examined in order to determine whether (i) an immediate diminution in performance could still be seen the next day and (ii) whether the treatment could achieve a relatively consistent and enduring enhancement of performance in the following days. Since this dose was also capable of inducing a short term deficit in performance, the effects of single administrations at lower doses of 0.1 and 1.0 mg/kg were examined.

All animals were rhesus macaques except one stumptail (*Macaca arctoides*). Details of the animal demographics are given with each set of results. It was desired to have younger animals in each study, however a preponderance of aged animals were studied, and females outnumbered males by 2 or 3 to one. The Spatial Delayed Response Task is established as one of the most reliable, sensitive, and valuable models in which to test spatial working memory in primates. The Spatial Delayed Response Task is implemented rigidly in a completely systematic format that is uniform within and between animals and between studies. The Spatial Delayed Response Task is designed to normalize performance across animals such they all normally perform at ~70% correct. The Spatial Delayed Response Task directly challenges the same spatial working memory circuitry in human and nonhuman primates, including dorsolateral prefrontal cortex, posterior parietal cortex and MD thalamus. The Spatial Delayed Response Task is sensitive to multiple neuropharmacological manipulations, whether administered locally or systemically, including dopaminergic, nicotinic, glutamatergic, and GABAergic agents. In this task one of several well locations are baited with food in view of the animal and then covered with identical plaques. An opaque shutter is then lowered for one of 5 variable delays, and then raised to allow the animal to make a response to one of the well locations to retrieve the food treat. Each animal is stabilized (65-75% correct ±≤2.5%) prior to commencing any administration by varying the number of wells and the lengths of the delay. Each testing session consists of 20 trials, 4 trials at each of 5 delays (distributed semi-randomly) ranging from 0, 1, 2, 3, and 4 N seconds, where N is incremented from 1 to 10 according to ability. The number of wells ranges for 2 to 7 and thus stability is achieved by gradually varying the number of wells and the N factor. Original baseline is achieved on initial training and is standardized over twenty sessions, thereafter an animal typically undergoes regular testing to ensure a reasonably stable baseline. An absolute minimum of three baseline sessions are required prior to any experimental condition. Animals are not food deprived but instead reward for correct responses with their most preferred treats (such as yoghurt raisins, gummy bears, and almonds) and then fed their normal ration of nutritional biscuits shortly after cognitive testing.

DPTQ was formulated as a suspension in 20% Captisol/PBS at pH8. Great care was taken to protect the compound in sonication and it was injected (at a volume of 0.2 ml/kg) via a 21G hypodermic needle (to avoid blockage) into the gluteus maximus within 2 hours of formulation (kept on ice). Vehicle was refrigerated in sterile injectable vials for up to one month. Animals were fully acclimated to all procedures prior to enrollment into any study. They were assigned on a readiness for study basis and where relevant, assignment was semirandom between vehicle and treatment arms. IM injections were performed in the animals' home cage 1 hour prior to cognitive testing. Testing is conducted in a sound attenuated chamber, based on the standard WGTA design, in dedicated procedure rooms adjacent to the animal housing.

Effects of a single administration of DPTQ were observed over a period of 14 days. Single doses were originally tested at 2.5 mg/kg in comparison to vehicle and the same vehicle data is reasonably applicable to the tests done later for single doses of 0.1 and 1.0 mg/kg DPTQ. Separate but overlapping baselines were used for the two conditions.

Figure 5:
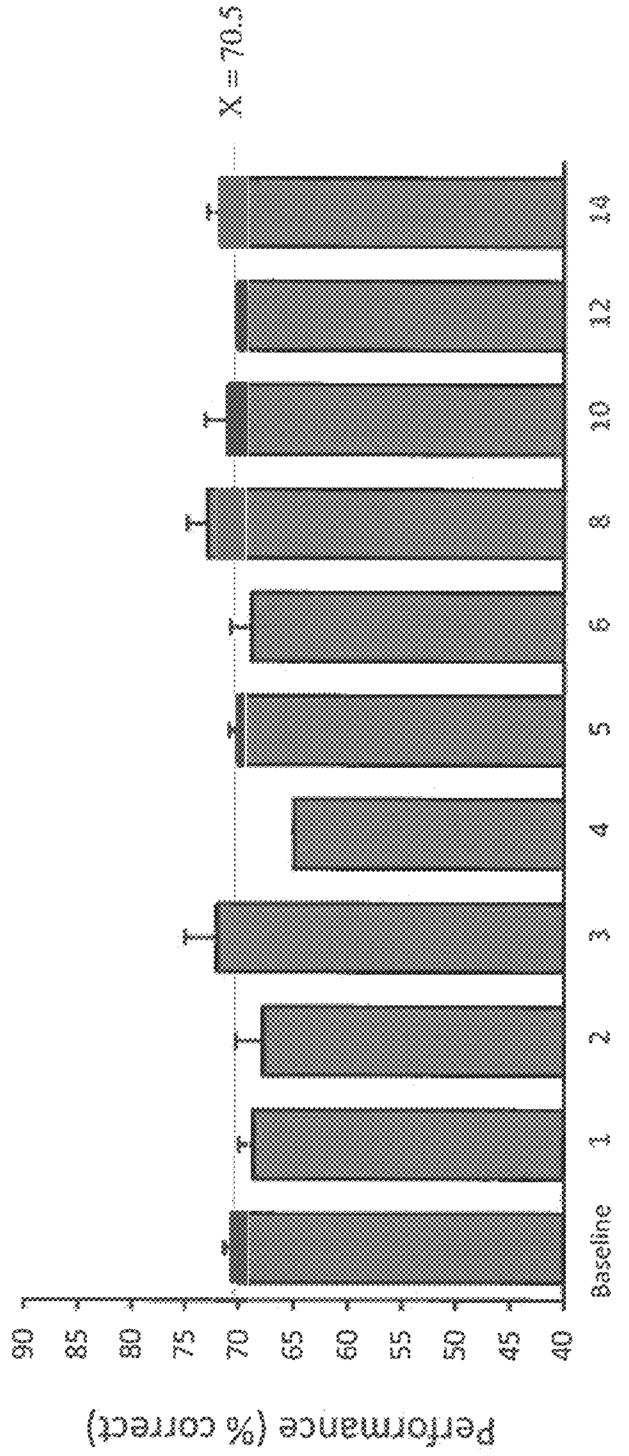
FIG. 5: Spatial working memory in the adult rhesus monkey: Acute administration of vehicle, data for a group of 10 animals, vehicle given on Day 1.

Vehicle data are shown in FIG. 5 for a group of 10 animals. Group changes in performance varied little from baseline over the next two weeks with the deviation for the group average reaching only 5%. Vehicle given on Day 1 produces no long lasting changes in cognitive performance.

Figure 6:
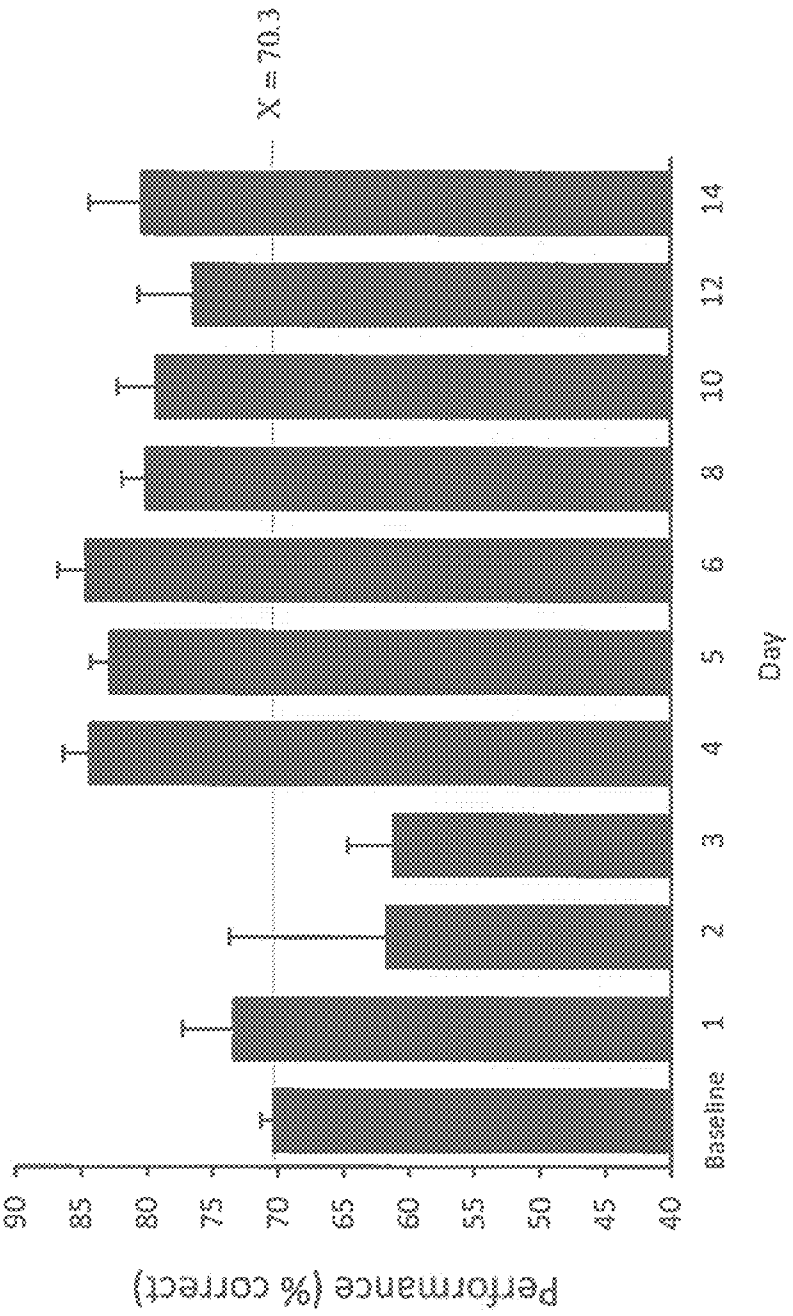
FIG. 6: Spatial working memory in the adult rhesus monkey: Acute administration of DPTQ at 2.5 mg/kg.

FIG. 6 shows Acute administration of DPTQ at 2.5 mg/kg. Treatment data are shown in FIG. 6 for a group of 9 animals. No immediate effect was seen on Day 1, but a diminution of performance was evident by Day 2 which became robust by Day 3 (ANOVA $F[1,14]=4.543$, $p=0.051$ vs baseline). This apparent impairment in cognition was immediately followed a sustained enhancement in cognition from Day 4 onwards (ANOVA $F[1,14]=45.061$, $p<0.001$ vs baseline). Of these 9 animals, 5 were aged and 4 were non-aged. By combining scores for Days 4, 5, and 6, we were able to compare between these two groups. No significant difference was seen between the two (ANOVA: $F[1,22]=0.066$, $p=0.799$). No acute effect of DPTQ was seen but an impairment of nearly 10% became evident on Day 3 followed by a prolonged enhancement starting from Day 4, again at close to 10%.

Figure 7:
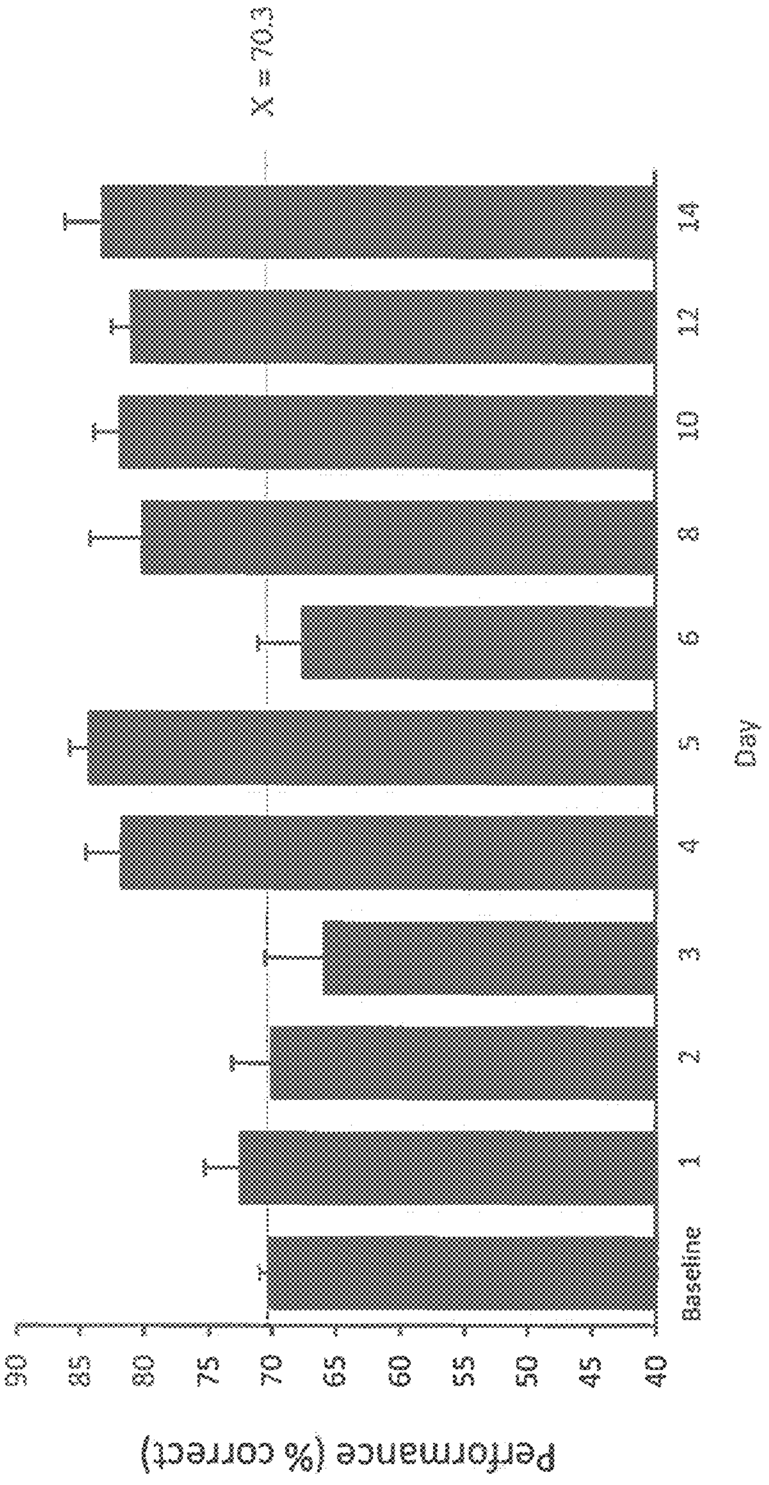
FIG. 7: Spatial working memory in the adult rhesus monkey: Effect of repeating the DPTQ dose of 2.5 mg/kg on Day 5.

The effects were also assessed of repeating administration of DPTQ on Day 5 of the observed period of 14 days. FIG. 7. shows the effects of repeating the dose of 2.5 mg/kg on Day 5. In this study, a dose of 2.5 mg/kg was administered acutely on Day 1 (1 hour prior to testing) and then either vehicle or an additional dose of 2.5 mg/kg was administered on Day 5 (immediately post testing). Animals were semi-randomly assigned to receive either the vehicle or treatment first on the repeated administration. When 2.5 mg/kg was administered again as the second dose on Day 5, we now observed a second subsequent dip in performance on Day 6 (FIG. 7). Though performance was not significantly below the level of baseline, it showed a substantial dip from the enhancement seen on the previous two days. Nevertheless, performance recovered within two days (ANOVA Day 4: $F[1, 10]=15.564$, $p=0.003$) and appeared to remain high for the week (ANOVA Day 10: $f[1,10]=25.912$, $p<0.001$). The early reduction in performance was seen again on Day 3 but was not significant. Following the acute dose on Day 1 the dip was seen again on Day 3 followed by the rebound enhancement on Day 4. However, following the repeat of the dose on Day 5, there is a distinctive drop in performance on Day 6 which then immediately yields to enhancement for the subsequent week.

Figure 8:
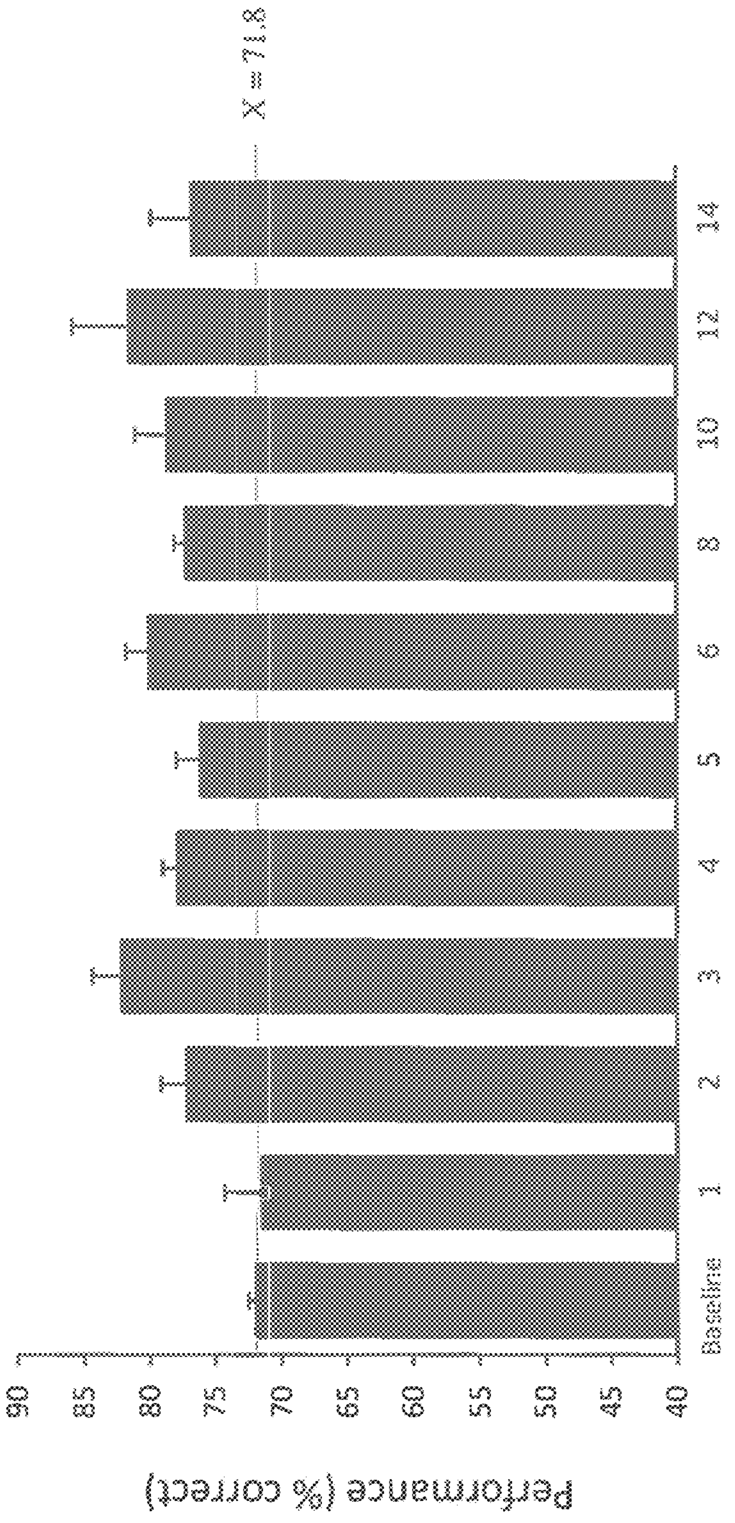
FIG. 8: Spatial working memory in the adult rhesus monkey: Effect of DPTQ when administered at a low dose of 0.1 mg/kg.

In order to better understand the dynamic range of these effects, administration of DPTQ at a low dose of 0.1 mg/kg was assessed. FIG. 8 shows the effects of DPTQ when administered at a low dose of 0.1 mg/kg. No sign of any diminution in performance was observed but the enhancement seen was modest. Interestingly, in a group of 10 animals, an absence of any deficit is observed on the third day and instead signs of a modest enhancement are observed which show some persistence over the course of the 2-week period (FIG. 8). Nevertheless Day 4 showed a significant improvement over baseline (ANOVA: $F[1,18]=24.132$, $p<0.001$). Within this group there were 6 aged and 4 non-aged animals. When there scores were compared at Day, no significant difference was seen between them (ANOVA F [1,8]=0.816, p=0.393.

Figure 9:
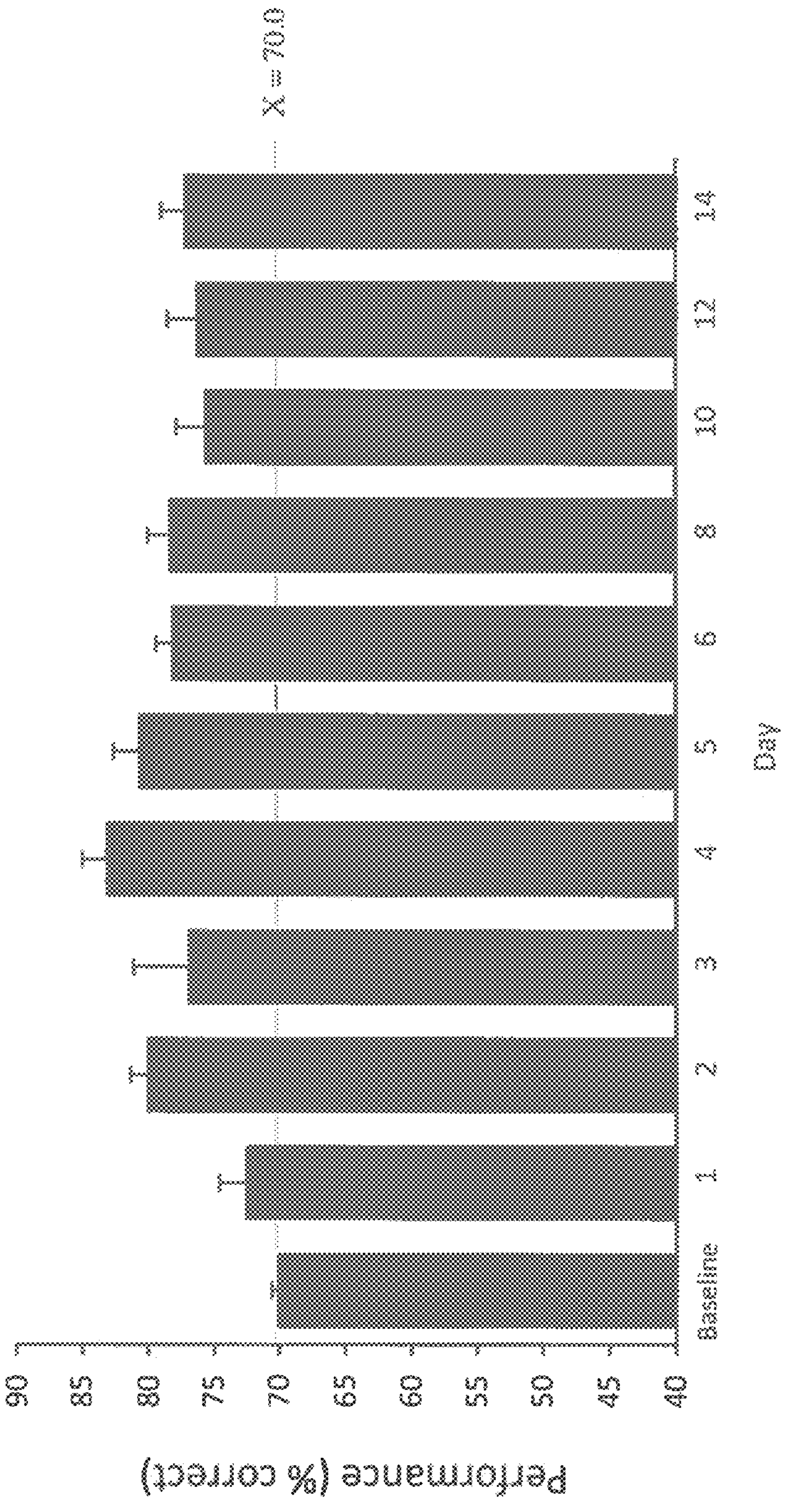
FIG. 9: Spatial working memory in the adult rhesus monkey: Effect of a dose of 1.0 mg/kg DPTQ on spatial working memory.

The effect of administration of DPTQ at a dose of 1.0 mg/kg on spatial working memory was assessed. As shown in FIG. 9, the early deficit was not evident and the enhancement appears to be stronger than for the 0.1 mg/kg dose and had significance on Day 5 (ANOVA F [1,14]=22.449, p<0.001). This group currently includes 6 aged ad 2 non-aged animals and an additional 2 non-aged animals which had not yet completed the study. No sign of any difference in scores between the two age groups were seen.

Thus, DPTQ at 1-10 mg/kg or lower may improve spatial working memory (as even the lowest dose studied showed significant improvement). Surprisingly pro-cognitive effects were observed at the low doses in the monkey of 0.1 and 1 mg/kg. IM. Higher doses of DPTQ of 2.5 mg/kg and above showed a slight dip in performance during the first 48 hours, but then a sustained positive effect lasting for at least to 14 days. These data provide evidence that DPTQ and/or LY3154207 may enhance cognitive performance in a time-dependent manner in primates. This primate cognition signal at 0.1 mg/kg (approximately equivalent to 1 mg oral dose of LY3154207 in humans) suggests that DPTQ can have pro-cognitive effects at lower doses without seeing evidence of initial loss of efficacy, thought to be due to over-activation. PK-PD projections estimate that the 1.0 mg/kg IM dose of DPTQ corresponds to 10 mg of LY3154207 in humans, and the 2.5 mg/kg dose of DPTQ corresponds to 25 mg of LY3154207 in humans. Phase I clinical data for the 15 mg dose of LY3154207 also showed a trend for better cognitive effects in the DSST task compared to higher doses.

These data, when viewed along with data from the phase I studies above, lead to the concept that dosing regimens of the present invention in the low dose range of 0.5 mg to 15 mg may provide effective enhancement of certain D1 signaling mediated responses, such as pro-cognitive effects, while avoiding higher levels of stimulation observed at higher doses, such as 20 mg-75 mg, such excessive wake promotion leading to insomnia, and or certain undesirable dose related cardiovascular effects such as pulse rate and blood pressure increases, as well as a decreased risk of drug-drug interactions with Cyp3A4 inhibitors. More particularly, it has been discovered that high dosing schedules of LY3154207, above 75 mg per day, can be associated with mild-to-moderate insomnia and agitation, and/or undesired cardiovascular effects, where doses above 75 mg may produce acute and/or persistent increases in BP and pulse rate. In Study HBEB, there was a linear and dose-dependent effect on sleep latency observed across the doses of 15 mg to 75 mg in sleep-deprived healthy subjects receiving a single dose of LY3154207. Activating adverse events such as insomnia are observed with a substantial increase in frequency above the 75 mg dose of LY3154207. Thus, in the present dosing regimens, the 75-mg dose represents a surprising and unpredictable separation in the desirable and undesirable effects of LY3154207.

Thus, the combined results of phase I human studies and primate studies have led to the concept of the present invention which provides improved clinical therapeutic dosing regimens and methods of using LY3154207, and/or pharmaceutical compositions thereof, for the treatment of dopaminergic central nervous system disorders. In particular, daily administration of LY3154207 provides an improved means to reduce signs and symptoms of dopaminergic central nervous system disorders in a clinically advantageous manner, such that safe, tolerable and effective relief clinical signs and symptoms is achieved.

In particular, the present invention further provides methods of using a low dose administration regimen that is believed to promote normalization of endogenous dopaminergic signaling in various dopamine mediated disease states, with a lower propensity for certain effects seen at higher doses, such as overstimulation, and less potential for development of tolerance and adverse effects associated with orthosteric D1 agonists. As a result of this normalizing effect, the LY3154207 clinical dosing regimens of the present invention, and in particular the low dose regimen, provide improved means for treatment of a range of dopamine mediated CNS deficits, with a surprising and unexpected combination of advantageous human clinical pharmacological efficacy, safety, and tolerability.

LY3154207 is currently in a phase 2 study for cognition in Lewy Body Dementias (NCT03305809). Results of this clinical trial may further support the surprising and unexpected advantages of the dosing regimens and doses for use in treatment of dopaminergic CNS disorders, such as LBD and PD and AD.

Example 3: Protocol for a Dose Regimen Study in Pd-Study HBEH, Also Referred to as "Presence"

Below is provided a protocol for a dose regimen study in PD with certain doses of the dosing regimens of the present invention. The skilled artisan will be able to apply the teachings of this Example 3 and other disclosures provided herein and conduct similar studies with additional doses and dosing regimens of the present invention.

Treatment of cognitive impairment due to PDD, that is well tolerated, remains an unmet medical need. By potentiating the response to the remaining brain dopamine (or administered levodopa) in subjects with PDD, a DIPAM should improve cognitive performance. In addition, a DIPAM should have a positive impact on the motor deficits, depression, and daytime sleepiness observed in subjects with PD.

LY3154207 may improve a variety of domains important to people with Lewy Body Dementias including signs of Parkinsonism, such motor symptoms, wakefulness, mood, and function. LY3154207 is being developed to treat the symptoms of cognitive impairment in dementias, where it may provide improvement in a relatively short period of chronic daily dosing (12 weeks or earlier). As a symptomatic agent, LY3154207 is important because even when progression slowing agents are available, patients will continue to suffer from the symptoms of dementia. By potentiating the response to the remaining brain dopamine (or administered leovdopa) in subjects with Parkinson's disease, LY3154207 is believed to improve cognitive performance, and provide treatment for Parkinson's disease subjects with neurocognitive impairment. Outcome goals for use of LY3154207 are improved cognition in PD dementia (PDD), inclusive of Dementia with Lewy Bodies (DLB), with additional benefits in motor and/or wakefulness.

The PRESENCE study is assessing three doses (10 mg. 30 mg, and/or 75 mg daily (or 50 mg based on interim analysis) (QD) oral dosing) of LY3154207 vs. placebo over 12 weeks of treatment. The primary outcome is a measure of cognition and we are assessing additional measures of cognition as key secondary endpoints. PRESENCE is a randomized placebo-controlled trial in individuals with Parkinson's disease dementia to evaluate the safety and efficacy of (three doses of study drug) LY3154207 in participants with mild-tomoderate Parkinson's disease dementia treated for 12 weeks. The primary outcome is a measure of cognition and additional measures of cognition are key secondary endpoints. The D1 PAM mechanism may impact a variety of domains important to people with Lewy Body Dementias, and measures of Parkinsonism (including motor symptoms), wakefulness, mood, and function are being assessed.

Study HBEH will include subjects who meet the revised MDS criteria for PD (Postuma et al. 2015) and mild-to-moderate dementia as defined by a decline in cognitive function, which in the opinion of the investigator has resulted in functional impairment and a MoCA score between 10 and 23 (Trzepacz et al. 2015). Per the revised MDS criteria, PDD can be diagnosed in the presence of dementia, regardless of the timing of dementia onset relative to PD diagnosis. Subjects diagnosed with dementia with Lewy bodies (DLBs) should be considered as also having PD if they meet the MDS PD criteria. Therefore, subjects may have dementia prior to, at the time of, or subsequent to the diagnosis of PD. Unlike registration trials of symptomatic therapies in PDD (Emre et al. 2004), the current study will include some subjects who would otherwise have met the traditional criteria (dementia prior to or within 1 year of motor onset) for DLB based on the timing of their dementia (Mckeith et al. 2005). This criterion was that the dementia occurs prior to or within 1 year of Parkinson's symptoms. The 1-year rule is arbitrary and based on the historical belief that PD was not associated with dementia: however, there is increasing controversy about the validity of this traditional approach to splitting the diagnoses (Berg et al. 2014). In support of the proposed approach, both disorders share a variety of clinical, genetic, and pathological features (Lippa et al. 2007: Postuma et al. 2009: Johansen et al. 2010). Both DLB and PDD are associated with similar impairments in cognition with predominant visuoperceptual abnormalities, improvement in memory with cues, and so on. Both are associated with prominent psychosis, neuroleptic sensitivity, and alterations in arousal. Prodromal features (e.g., rapid eye movement [REM] sleep behavior disorder, olfactory loss) are the same in both conditions. Non-motor symptoms with depression, anxiety, autonomic dysfunction and sleep disturbances occur with similar relative frequency in both. The same genetic mutations (alpha-synuclein duplications, glucocerebrosidase mutations) are associated with the development of either condition. Finally, they have a shared pathology with alpha-synuclein and Lewy body formation in the brain stem and cortex. Therefore, the Study HBEH meets current thinking about PDD and DLB that, apart from the timing of cognitive impairment, they are clinically and pathologically indistinguishable and would likely respond to similar therapeutic approaches (Aarsland et al. 2004; Ballard et al. 2006). Placebo is included as the control, in a blinded manner for investigator and site staff and subjects, to allow for an unbiased assessment of the safety data generated, which will allow for a more robust comparison between LY3154207 and placebo data. Comparison of 3 dosage levels of LY3154207 was chosen to evaluate dosage exposure response for safety and efficacy. Initial visits (Visit 3 to Visit 7) were selected to occur at a weekly interval to provide a detailed evaluation of the efficacy and safety of LY3154207 during the initial treatment. A dosing duration of 12 weeks was selected, as it is estimated to be the minimum duration where a beneficial effect on cognition may be observed.

The primary objective is to test the hypothesis that LY3154207 administered at 10 mg, 30 mg, and/or 75 mg daily (or 50 mg based on interim analysis) (QD) oral dosing for 12 weeks will result in a significant improvement in cognition in subjects with mild-to-moderate PDD compared with placebo. Primary endpoints are changes in the CoA composite score of the CDR-CCB from baseline to Week 12. Secondary objectives are described below.

| Secondary efficacy objectives | Secondary efficacy endpoints |
|---|---|
| To evaluate the global efficacy of LY3154207 | ADCS-CGIC score from baseline to Week 12 |
| To evaluate the efficacy of LY3154207 on cognitive outcomes | Change in the CDR-CCB PoA composite score from baseline to Week 12 |
| To evaluate the efficacy of LY3154207 on cognitive outcomes | Change in the ADAS-Cog13 score from baseline to Week 12 |
| To evaluate the efficacy of LY3154207 on cognitive outcomes | Change in the MoCA score from screening to Week 12 |
| To evaluate the efficacy of LY3154207 on neuropsychiatric symptoms | Change in the NPI total and individual items scores from baseline to Week 12 |
| To evaluate the effect of LY3154207 on daytime sleepiness | Change in the ESS score from baseline to Week 12 |
| To evaluate the effect of LY3154207 on PD severity | Change in the MDS-UPDRS total score (sum of Parts I-III) from baseline to Week 12 |
| To evaluate the efficacy of LY3154207 on functional outcome | Change in the PDAQ-15 total score from baseline to Week 12 |
| To evaluate the effect of LY3154207 on verbal fluency | Change in D-KEFS Verbal Fluency test score from baseline to Week 12 |
| **Safety objectives** | **Safety endpoints** |
| To evaluate the effect of LY3154207 on acute changes of vital signs on the first day of dosing | Number of subjects who met the potentially clinically significant vital signs criteria at 3 consecutive time points at Visit 3 (Day 1 stopping rules) |
| To evaluate the effect of LY3154207 on SBP on the first day of dosing | Change in in-clinic SBP from 0 up to 8 hours post dose on the first day of study drug dosing |
| To evaluate the effect of LY3154207 on pulse rate on the first day of dosing | Change in in-clinic pulse rate from 0 up to 8 hours post dose on the first day of study drug dosing |
| To evaluate the effect of LY3154207 on SBP from baseline to Week 12 | Change in in-clinic mean SBP at baseline to mean SBP at Week 12 |
| To evaluate the effect of LY3154207 on pulse rate from baseline to Week 12 | Change in in-clinic mean pulse rate at baseline to mean pulse rate at Week 12 |
| **Pharmacokinetics objectives:** | **Pharmacokinetics objectives:** |
| To assess the PK of LY3154207 in a population of subjects with mild-to-moderate dementia due to PD | Steady-state trough plasma concentrations of LY3154207 at Week 12 |

Abbreviations: ADAS-Cog13=13-item Alzheimer's Disease Assessment Scale-Cognitive subscale; ADCS-CGIC=Alzheimer's Disease Cooperative Study-Clinician Global Impression of Change; CDR-CCB=Cognitive Drug Research-Computerized Cognition Battery; CoA=Continuity of Attention; D-KEFS=Delis-Kaplan Executive Function System; ESS=Epworth Sleepiness Scale; MDS-UPDRS=Movement Disorder Society's Unified Parkinson's Disease Rating Scale; MoCA=Montreal Cognitive Assessment; NPI=Neuropsychiatric Inventory; PD=Parkinson's disease; PDD=Parkinson's disease dementia; PDAQ-15=Penn Parkinson's Daily Activities Questionnaire-15; PK=pharmacokinetics; PoA=Power of Attention; QD=once a day; SBP=systolic blood pressure.

REFERENCES

Postuma R B, Berg D, Stern M, Poewe W, Olanow C W, Oertel W, Obeso J, Marek K, Litvan I, Lang A E, Halliday G, Goetz C G, Gasser T, Dubois B, Chan P, Bloem B R, Adler C H, Deuschl G. MDS clinical diagnostic criteria for Parkinson's disease. Mov Disord. 2015;30 (12): 1591-1601.

Trzepacz P T, Hochstetler H, Wang S, Walker B, Saykin A J; Alzheimer's Disease Neuroimaging Initiative. Relationship between the Montreal Cognitive Assessment and Mini-mental State Examination for assessment of mild cognitive impairment in older adults. BMC Geriatr. 2015; 15:107.

Emre M, Aarsland D, Albanese A, Bymne E J, Deuschl G, De Deyn P P, Durif F, Kulisevsky J, van Laar T, Lees A, Poewe W, Robillard A, Rosa M M, Wolters E, Quarg P, Tekin S, Lane R. Rivastigmine for dementia associated with Parkinson's disease. N Engl J Med. 2004: 351 (24): 2509-2518.

McKeith I G, Dickson D W, Lowe J, Emre M, O'Brien J T, Feldman H, Cummings J, Duda J E, Lippa C, Perry E K, Aarsland D, Arai H, Ballard C G, Boeve B, Burn D J, Costa D, Del Ser T, Dubois B, Galasko D, Gauthier S, Goetz C G, Gomez-Tortosa E, Halliday G, Hansen L A, Hardy J, Iwatsubo T, Kalaria R N, Kaufer D, Kenny R A, Korczyn A, Kosaka K, Lee V M, Lees A, Litvan I, Londos E, Lopez O L, Minoshima S, Mizuno Y, Molina J A, Mukaetova-Ladinska E B, Pasquier F, Perry R H, Schulz J B, Trojanowski J Q, Yamada M: Consortium on DLB. Diagnosis and management of dementia with Lewy bodies: third report of the DLB Consortium. Neurology. 2005: 65 (12): 1863-1872.

Berg D, Postuma R B, Bloem B, Chan P, Dubois B, Gasser T, Goetz C G, Halliday G M, Hardy J, Lang A E, Litvan I, Marek K, Obeso J, Oertel W, Olanow C W, Poewe W, Stern M, Deuschl G. Time to redefine PD? Introductory statement of the MDS Task Force on the definition of Parkinson's disease. Mov Disord. 2014: 29 (4): 454-462.

Lippa C F, Duda J E, Grossman M, Hurtig H I, Aarsland D, Boeve B F, Brooks D J, Dickson D W, Dubois B, Emre M, Fahn S, Farmer J M, Galasko D, Galvin J E, Goetz C G, Growdon J H, Gwinn-Hardy K A, Hardy J, Heutink P, Iwatsubo T, Kosaka K, Lee V M, Leverenz J B, Masliah E, McKeith I G, Nussbaum R L, Olanow C W, Ravina B M, Singleton A B, Tanner C M, Trojanowski J Q, Wszolek Z K: DLB/PDD Working Group. DLB and PDD boundary issues: diagnosis, treatment, molecular pathology, and biomarkers. Neurology. 2007: 68 (11): 812-819.

Postuma R B, Gagnon J F, Vendette M, Montplaisir J Y. Idiopathic REM sleep behavior disorder in the transition to degenerative disease. Mov Disord. 2009: 24 (15): 2225-2232.

Johansen K K, White L R, Sando S B, Aasly J O. Biomarkers: Parkinson disease with dementia and dementia with Lewy bodies. Parkinsonism Relat Disord. 2010: 16 (5): 307-315.

Aarsland D, Ballard C G, Halliday G. Are Parkinson's disease with dementia and dementia with Lewy bodies the same entity? J Geriatr Psychiatry Neurol. 2004: 17 (3): 137-145.

American Psychiatric Association. Diagnostic and statistical manual of mental disorders. 5th ed. Washington, D C: 2013.

Ballard C, Ziabreva I, Perry R, Larsen J P, O'Brien J, McKeith I, Perry E, Aarsland D. Differences in neuropathologic characteristics across the Lewy body dementia spectrum. Neurology. 2006: 67 (11): 1931-1934.

Yesavage J A, Brink T L, Rose T L, Lum O, Huang V, Adey M., Leirer V O. Development and validation of a geriatric depression screening scale: A preliminary report. J Psychiatr Res. 1983:17:37-49.

Sheikh J I, Yesavage J A. Geriatric Depression Scale (GDS): Recent evidence and development of a shorter version. Clin Gerontologist. 1986:5:165-173.

Summary of Study Design: Study 17S-MC-HBEH (HBEH) is a multicenter, randomized, double-blind, parallel-group, placebo-controlled, fixed-dosage, Phase 2a study comparing 3 dosages of LY3154207 (10, or 30, or 75 mg administered orally [or 50 mg based on interim analysis] once a day [QD]) with placebo over 12 weeks in subjects with mild-to-moderate PDD. The study includes a Screening Period (Visits 1 to 2) of a minimum of 7 days and up to 14 days, a Pretreatment Period of a minimum of 11 days and up to 17 days (Visits 2 to 3), a 12-week Treatment Period (Visits 3 to 11), and a 14-day Safety Follow-Up Period (Visits 11 to 801 or early termination [ET]/discontinuation [DC] visit to Visit 801). Subjects who meet entry criteria will be randomized in a 1:1:1:1 ratio to LY3154207 (10 or 30 or 75 mg QD) or placebo. The primary objective of the study is to test the hypothesis that LY3154207 administration for 12 weeks will result in a significant improvement in cognition as measured by the change from baseline to Week 12 in the Continuity of Attention (CoA) composite score of the Cognitive Drug Research Computerized Cognition Battery (CDR-CCB), in subjects with mild-to-moderate PDD, compared to placebo. The CoA has demonstrated a significant treatment effect in previous trials in subjects with PDD (Wesnes et al. 2005: Rowan et al. 2007).

Treatment Arms and Duration: Study HBEH involves a comparison of LY3154207 10 mg, 30 mg, and 75 mg (or 50 mg based on interim analysis) administered orally QD with placebo over 12 weeks. Number of subjects: Approximately 400 subjects will be screened to achieve 340 randomized and an estimated total of 85 evaluable subjects per treatment group.

Statistical Analysis:

Efficacy Analysis: All subjects in the evaluable patient population (EPP) will be considered for the efficacy analysis. The primary analysis on CoA will occur when all subjects complete 12 weeks of treatment. The analysis of CoA will utilize a Bayesian MMRM model. The Bayesian analysis may use uninformative priors for all terms in the model. These will be diffuse Normal distributions centered on zero. Priors for variance will follow an inverse gamma distribution. Further details of the Bayesian analysis will be provided in the SAP. The MMRM model will account for longitudinal data assessed throughout the study, after 1, 2, 4, 6, 8, 10, and 12 weeks of dosing. The change of CoA from the baseline to Week 12 will be the dependent variable. The model will comprise fixed (baseline value, treatment, visit) and random effects (subject) and the interaction terms (treatment by visit, baseline value by visit). Unstructured variance structure will be applied in the model, but if it fails to converge, other suitable structures will be investigated. The primary comparison will be the contrast (difference in least squares mean) between treatments and placebo for the Week 12 change from baseline. The secondary efficacy outcomes: the change from baseline at 12-week time point of total scores (or composite values) of Alzheimer's Disease Cooperative Study-Clinician Global Impression of Change (ADCS-CGIC), CDR-CCB Power of Attention (PoA), 13-item Alzheimer's Disease Assessment Scale-Cognitive subscale (ADAS-Cog13), Montreal Cognitive Assessment (MoCA), Neuropsychiatric Inventory (NPI), Epworth Sleepiness Scale (ESS), Movement Disorder Society's Unified Parkinson's Disease Rating Scale (MDS-UPDRS), Penn Parkinson's Daily Activities Questionnaire 15 (PDAQ-15), and Delis-Kaplan Executive Function System (D-KEFS) will follow the same analysis method as above. Missing records in some scales (e.g., ADAS-Cog) will be imputed as detailed in the statistical analysis plan. For the scales where the imputation is not done, if any item is missing, any total or sum involving that item will be considered missing. No adjustment for multiple comparisons will be made.

Safety Analysis: Safety analyses are based on the safety population and analysis will include listings and/or summaries of the following: adverse events (AEs), serious adverse events (SAEs), treatment-emergent adverse events (TE-AEs), laboratory measures, vital signs, electrocardiogram readings and number of subjects who met the potentially clinically significant vital signs criteria at 3 consecutive time points at Visit 3 (Day 1 stopping rules). Mixed-model repeated measures analysis will be used to compare the change in in-clinic blood pressure (BP) and pulse rate from pretreatment up to 8 hours post dose measured on the first day of study drug dosing (V3). Two baselines will be considered in the change from baseline analyses: the V3 pretreatment value and the time-matched baselines from Visit 2 (hourly value 0 to 6 hours). For the second baseline, the V3, 7- and 8-hour time points will use the V2 6-hour time point as their baseline value. A separate change from baseline analysis will be completed for each baseline approach. Mixed-model repeated measures analyses will also be used to compare change in in-clinic BP and pulse rate from V2 (daily average 0 to 6 hours) to Week 6/Visit 8 and Week 12/Visit 11 (daily average 0 to 6 hours), to evaluate the change in BP and pulse rate over 12 weeks of dosing.

Pharmacokinetics (PK): Pharmacokinetic analyses will be conducted on subjects who receive at least 1 dose of the study drug and have 1 measurable concentration. A model-based approach may be implemented using nonlinear mixed effects modeling (NONMEM) or other appropriate software to estimate PK parameters.

Additional endpoints and biomarker data collected during the study may be evaluated in an exploratory manner.

Interim Analysis: Safety interim analyses will be conducted on the number of subjects on each treatment who met the potentially clinically significant vital signs criteria at 3 consecutive time points at Visit 3 (Day 1 stopping rules). This will be done after 50, 100, and 150 subjects have completed Visit 3. If there is >60% probability that the difference in rate of subjects meeting Day 1 stopping rules for 75 mg LY3154207 compared to placebo is >0.3, the 75-mg dose level will be replaced with 50 mg for the subsequently enrolled subjects. Those already on 75-mg dose and passed the Day 1 stopping rules will remain on 75 mg. In the event of an unacceptable rate of subjects meeting Day 1 stopping rules at other doses, adjustments to doses may be made for subsequently randomized subjects at the discretion of the Internal Assessment Committee (IAC). Additional efficacy analyses may be conducted at the time of these safety interim analyses. A safety and efficacy interim analysis will be conducted when 170 randomized subjects have completed Visit 11 (Week 12) assessments. All potential efficacy analyses may be used for internal decision making, but are not planned to stop the study.

Study HBEH will include men and women aged 40 to 85 years with mild-to-moderate PDD. Subjects are eligible to be included in the study only if they meet all the following criteria at enrollment (Visit 1) (note that inclusion criteria [6] to must be met or at an additional visit [s]):

Type of Subject and Disease Characteristics: [1] Male and female subjects aged 40 to 85 years (inclusive). [2] Have idiopathic PD per MDS criteria (Postuma et al. 2015) with at least 2 years of PD symptoms. [3] Have dementia as defined by a decline in cognitive function, which in the opinion of the investigator has resulted in functional impairment. [4] Have a MoCA score of 10 to 23 at the time of screening. [5] Are Modified Hoehn and Yahr Stages 1 to 4. [6] Have a BP or pulse rate at Visit 1 and Visit 3, as determined by 3 sequential BP/pulse rate measurements in the seated position:

For Subjects <60 years old: a mean systolic blood pressure (SBP) less than or equal to 140 mmHg, a mean diastolic BP less than or equal to 90 mmHg, and a mean pulse rate less than or equal to 90 beats/min in the seated position, and each of the 3 SBP measurement must be less than 180 mmHg.

For Subjects ≥60 years old: a mean SBP less than or equal to 150 mmHg, a mean diastolic BP less than or equal to 90 mmHg, and a mean pulse rate less than or equal to 90 beats/min in the seated position, and each of the 3 SBP measurement must be less than 180 mmHg.

The following PD severity and cognitive assessments, as well as the Columbia-Suicide Severity Rating Scale (C-SSRS), will be done at Visit 1 as part of the subject eligibility evaluation: Movement Disorder Society (MDS) Clinical Diagnostic Criteria for Parkinson's disease Enrolled individuals will meet MDS criteria for clinically probable PD (Postuma et al. 2015). Subjects must have bradykinesia with either rest tremor and/or rigidity. Subjects must not have any absolute exclusion criteria described in Appendix 5. Subjects must not have the presence of greater than 2 red flags: if 1 red flag is present then it must be offset by 1 supportive criterion and if 2 red flags are present it must be offset by 2 supportive criteria.

In addition to meeting criteria for PD, subjects must meet criteria for dementia as described below (Montreal Cognitive Assessment [MoCA] Scale). The MDS criteria do not consider dementia as an exclusion criterion for PD and therefore there will be no restriction on the timing of dementia relative to the development of the motor features of PD.

Modified Hoehn and Yahr Scale: Enrolled individuals must be Hoehn and Yahr Stage 1 to Stage 4 at screening. The Hoehn and Yahr Scale (Hoehn and Yahr 1967) is used to describe the symptom progression of PD. The scale was originally described in 1967 and included Stages 1 through 5. It has since been modified with the addition of Stages 1.5 and 2.5 to account for the intermediate course of PD. The modified Hoehn and Yahr scale is as follows: Stage 0): No signs of disease, Stage 1: Unilateral disease, Stage 1.5: Unilateral plus axial involvement, Stage 2: Bilateral disease, without impairment of balance, Stage 2.5: Mild bilateral disease, with recovery on pull test, Stage 3: Mild-to-moderate bilateral disease: some postural instability: physically, independent, Stage 4: Severe disability: still able to walk or stand unassisted, Stage 5: Wheelchair bound or bedridden unless aided.

Montreal Cognitive Assessment Scale: Enrolled individuals must have a MoCA score of 10 to 23 at screening.

Geriatric Depression Scale: Enrolled individuals must have a Geriatric Depression Scale-Short Form (GDS-S) score of ≤6 at screening. The GDS is a site-administered questionnaire of depression in older adults (Yesavage et al. 1983). Users respond in a "Yes/No" format. Originally developed as a 30-item scale (Long Form), it has since been shortened to a 15-item scale (Short Form), which can be completed in approximately 5 to 7 minutes (Sheikh and Yesavage 1986). Of the 15 items, 10 are indicative of depression when answered "Yes" and 5 are indicative of depression when answered "No."

Columbia-Suicide Severity Rating Scale-Children's Version: The C-SSRS is a scale that captures the occurrence, severity, and frequency of suicide-related thoughts and behaviors during the corresponding assessment period. The C-SSRS, included here as a screening assessment, is described in detail in Section 9.4.4. The C-SSRS "Baseline" version will be used at screening, and the findings will constitute the baseline assessment. The C-SSRS will be administered to the subject after the cognitive and functional assessments. Responses from subject will be considered when administering the scale. If it is determined that the subject has suicidal ideation or behavior at this baseline assessment, then the subject will not be randomized and will be discontinued from the study.

Example 4 Protocol for a Dose Regimen Study in AD

LY3154207 is believed to be effective in improving cognitive dysfunctions in Alzheimer's disease through activation of cortical neurons, enhanced synaptic plasticity and neurotransmitter release. Other potential effects of LY3154207 such as reduced daytime sleepiness, improved mood and/or apathy, and goal-directed behaviors leading to reduced apathy (via activation of cortical and striatal D1 receptors) would also be beneficial in an Alzheimer's disease population. Using methods known to the skilled artisan, utility in AD may be demonstrated in mild to moderate AD patients (MMSE 13-26), in clinical studies of 24 weeks or more duration, where patients are administered doses of about 0.5 mg to about 75 mg, up to a maximum total dose of 75 mg per day, of LY3154207 or pharmaceutical composition thereof, and efficacy, safety and tolerability are assessed by methods known to the skilled artisan, including for example ADAS-Cog13, MMSE, ADCS-CGIC, ADCS-ADL, AD-QOL, NPI, and ESS.

Example 5: Other Dopaminergic CNS Disorders

Utility in a variety of other dopaminergic CNS disorders including Vascular Dementia, Schizophrenia, ADHD, Depression, Autism, chronic musculoskeletal pain, fibromyalgia, cognitive impairment disorders, sleep disorders, excessive daytime sleepiness, narcolepsy, shift work disorder, traumatic brain injury, chronic traumatic encephalopathy, obesity and appetite regulation, mood disorders, lethargy, apathy, and addiction disorders, may be demonstrated by clinical studies wherein patients with said disorders are administered doses of about 0.5 mg to about 75 mg, up to a maximum total dose of 75 mg per day, of LY3154207 or pharmaceutical composition thereof, and efficacy, safety and tolerability are assessed by methods known to the skilled artisan.

We claim:

1. A method of treating a dopaminergic central nervous system disorder in a patient in need thereof, the method comprising administering to the patient a dose of 10 mg to 75 mg, up to a maximum total dose of 75 mg per day, of LY3154207 or a pharmaceutical composition thereof.

2. The method of claim 1, comprising administering to the patient a dose of 10 mg to 50 mg, up to a maximum total dose of 50 mg per day, of LY3154207 or a pharmaceutical composition thereof.

3. The method of claim 1, comprising administering to the patient a dose per day selected from the group consisting of 10 mg, 15 mg, 20 mg, 25 mg, 30 mg, 50 mg, and 75 mg, of LY3154207, or a pharmaceutical composition thereof.

4. The method of claim 1, comprising administering to the patient a dose of 25 mg per day of LY3154207 or a pharmaceutical composition thereof.

5. The method of claim 1, comprising administering to the patient a dose of 10 mg per day of LY3154207 or a pharmaceutical composition thereof.

6. The method of claim 1, comprising administering to the patient a dose of 15 mg per day of LY3154207 or a pharmaceutical composition thereof.

7. The method of claim 1, comprising administering to the patient a dose of 20 mg per day of LY3154207 or a pharmaceutical composition thereof.

8. The method of claim 1, comprising administering to the patient a dose of 50 mg per day of LY3154207 or a pharmaceutical composition thereof.

9. The method of claim 1, comprising administering to the patient a dose of 75 mg per day of LY3154207 or a pharmaceutical composition thereof.

10. The method of claim 1, wherein the dopaminergic central nervous system disorder is selected from the group consisting of Lewy body dementia (LBD), Parkinson's disease, Alzheimer's disease, vascular dementia, schizophrenia, ADHD, depression, chronic musculoskeletal pain, fibromyalgia, cognitive impairment disorders, excessive daytime sleepiness, narcolepsy, shift work disorder, traumatic brain injury, chronic traumatic encephalopathy, obesity and appetite regulation, mood disorders, lethargy, apathy, and addiction disorders.

11. The method of claim 1, wherein the dopaminergic central nervous system disorder is Parkinson's disease.

12. The method of claim 1, wherein the patient meets the revised Movement Disorder Society criteria for Parkinson's disease and mild-to-moderate dementia as defined by a decline in cognitive function with an Montreal Cognitive Assessment Scale score between 10 and 23.

13. The method of claim 1, wherein the dopaminergic central nervous system disorder is Alzheimer's disease.

14. The method of claim 1, wherein the dopaminergic central nervous system disorder is obesity.

15. The method of claim 1, wherein the patient is administered LY3154207 once a day for a pretreatment period having a minimum of 11 days and a maximum of 17 days.

16. The method of claim 11 comprising administering to the patient a dose of 25 mg per day of LY3154207 or a pharmaceutical composition thereof.

17. The method of claim 11 comprising administering to the patient a dose of 50 mg per day of LY3154207 or a pharmaceutical composition thereof.

18. The method of claim 13 comprising administering to the patient a dose of 25 mg per day of LY3154207 or a pharmaceutical composition thereof.

19. The method of claim 13 comprising administering to the patient a dose of 50 mg per day of LY3154207 or a pharmaceutical composition thereof.

20. The method of claim 1, wherein the dopaminergic central nervous system disorder is Lewy body dementia.

21. The method of claim 20 comprising administering to the patient a dose of 25 mg per day of LY3154207 or a pharmaceutical composition thereof.

22. The method of claim 20 comprising administering to the patient a dose of 50 mg per day of LY3154207 or a pharmaceutical composition thereof.

23. The method of claim 1, wherein the dopaminergic central nervous system disorder is dementia with Lewy bodies.

24. The method of claim 23 comprising administering to the patient a dose of 25 mg per day of LY3154207 or a pharmaceutical composition thereof.

25. The method of claim 23 comprising administering to the patient a dose of 50 mg per day of LY3154207 or a pharmaceutical composition thereof.

* * * * *